(12) United States Patent
Linares

(10) Patent No.: US 8,529,624 B2
(45) Date of Patent: Sep. 10, 2013

(54) BREAST AND NIPPLE IMPLANT CONSTRUCTIONS

(75) Inventor: Miguel A. Linares, Bloomfield Hills, MI (US)

(73) Assignee: Miguel A. Linares, Bloomfield Hills, MI (US)

( * ) Notice: Subject to any disclaimer, the term of this patent is extended or adjusted under 35 U.S.C. 154(b) by 0 days.

(21) Appl. No.: 13/313,415

(22) Filed: Dec. 7, 2011

(65) Prior Publication Data
US 2012/0143330 A1 Jun. 7, 2012

Related U.S. Application Data

(60) Provisional application No. 61/420,634, filed on Dec. 7, 2010.

(51) Int. Cl.
*A61F 2/12* (2006.01)
(52) U.S. Cl.
USPC .................................................... 623/8; 623/7

(58) Field of Classification Search
USPC ........................................................ 623/7, 8
See application file for complete search history.

(56) References Cited

U.S. PATENT DOCUMENTS 4,778,465 A * 10/1988 Wilkins ............................ 623/8
5,713,959 A * 2/1998 Bartlett et al. .................... 623/8

* cited by examiner

*Primary Examiner* — Thomas J Sweet
*Assistant Examiner* — Krutanjali M Shah
(74) *Attorney, Agent, or Firm* — Gifford, Krass, Sprinkle, Anderson & Citkowski, P.C.; Douglas J. McEvoy

(57) ABSTRACT

A breast implant having a fluid holding and flexible membrane body. A plurality of tabs are located along a perimeter extending side or underside of the body and are adapted for engaging a muscle layer upon which the body is supported. Inner defining partitioning walls establishing a plurality of chambers and include vents at inner locations in order to manage the transfer of fluid between the chambers. A corresponding nipple implant body also includes a reservoir chamber and an interconnected nipple extender chamber via a stop or check valve positioned therebetween, with the outermost nipple extender chamber being repositionable along a surface of the implant body.

6 Claims, 23 Drawing Sheets

BREAST AND NIPPLE IMPLANT CONSTRUCTIONS

CROSS REFERENCE TO RELATED APPLICATIONS

The present application claims the priority of U.S. Provisional Application Ser. No. 61/420,634 filed Dec. 7, 2010.

FIELD OF THE INVENTION

The present invention relates generally to reconstructed breast implants, such as following breast removal normally associated with mastectomy procedures. More specifically, the present invention discloses a collection of both breast and nipple implants, arranged both in combination and separately, and which provide more natural and dynamic performance aspects similar to natural tissue and as opposed to prior implant designs.

DESCRIPTION OF THE PRIOR ART

Breast and nipple implants are utilized in cosmetic and/or other types of reconstructive surgery, such as following cancer driven surgical procedures including single or double breast mastectomy. Often constructed of silicone or like material, a shortcoming of such previously known implant designs includes their relatively artificial and lifeless appearance.

SUMMARY OF THE PRESENT INVENTION

The present invention discloses each of individual breast and nipple implants, installed separately or in combination, and which overcomes many of the shortcomings associated with prior art implant designs. Specifically, the individual implant assemblies each incorporate fluid communicating chambers for selectively inflating and deflating certain aspects of the implant. In this fashion, the implants can be manipulated in a way so as to replicate certain auto arousal functions associated with normal breast tissue, such as attendant with sexual activity occurring between couples, this further providing positive psychological reinforcement to the (typically female) individual and which is often lacking in the instance of prior implant constructions.

A first breast implant can include a fluid holding and flexible membrane body. A plurality of tabs are located along at least one of perimeter extending side or underside location of the body and which is adapted for engaging a muscle layer upon which the body is supported. The tabs can each further include any of staples, barbs, and tangs for engaging the muscle layer and may further be constructed of a self dissolvable composition.

The implant body can also include a plurality of inner defining partitioning walls for establishing a plurality of chambers and can include any arrangement of vents established at given wall locations in order to manage the transfer of fluid between the chambers. The body can also be constructed of any of a plasticized, silicone or sponge construction and can incorporate any arrangement of arcuate extending membrane supports.

Additionally or alternatively to the breast implant, a corresponding nipple implant body can include a reservoir chamber and an interconnected nipple extender chamber via a stop or check valve positioned therebetween. The reservoir chamber can also include at least one of a plasticized, silicone or sponge construction, with the outermost nipple extender chamber being repositionable along a surface of the implant body.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

As previously described, the present invention discloses a collection of both breast and nipple implants, arranged both in combination and separately, and which provide more natural and dynamic performance aspects similar to natural tissue and as opposed to prior implant designs. The objectives of the variants described herein includes improvements both to the construction and manner of attaching/anchoring of the underlying breast implant, such as to the subcutaneous and supporting muscle layer of the patient, as well as the provision and arrangement of a combination or separate nipple implant, such further which includes the ability to simulate auto-arousal physiological responses through the incorporation of a fluid actuating and extendable nipple chamber in communication with a fluid reservoir supporting chamber. In this fashion, the present invention provides a more life like and improved nipple construction which, when installed in combination with the underlying breast implant, provides a number of benefits along with assisting in the mental and psychological rehabilitation of the patient.

Figure 1:
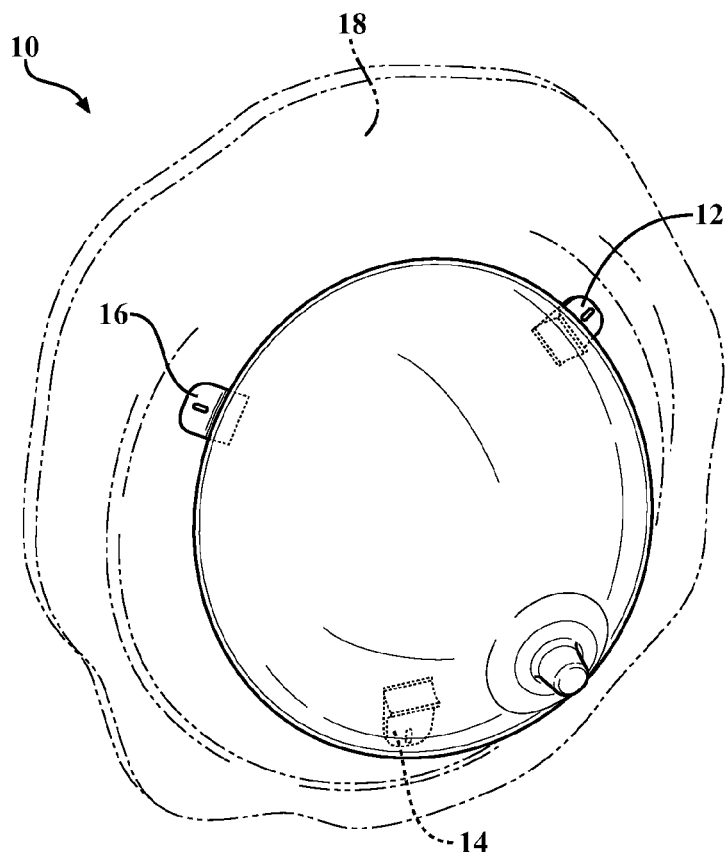
FIG. 1 is a localized perspective and environmental view of a breast implant according to one variant and which is securable underneath an outermost skin layer depicted in partial phantom by perimeter edge spaced and underside engaging tabs.

Referring initially to FIG. 1, a generally perspective and environmental view is depicted at 10 of a breast implant according to one variant, such as which is implantable following a surgical procedure known as a mastectomy or otherwise implanted in order to replace or reconstruct a missing breast. As will be described in further detail, the implant 10 is typically constructed as a flexible polymeric material filled with a fluid of given viscosity and which is securable underneath, or subcutaneously, relative to the outer skin (not shown).

Figure 2:
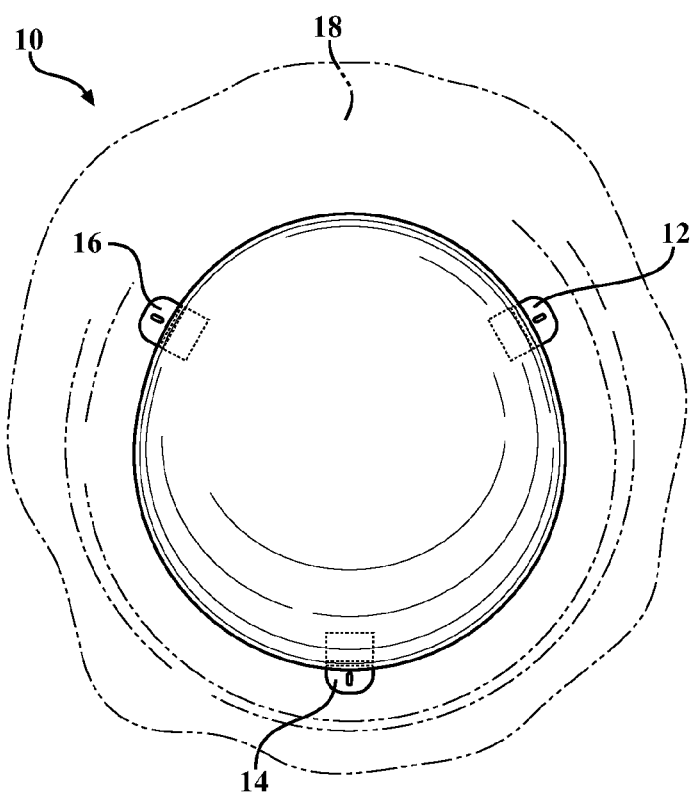
FIG. 2 is a plan view of the implant in FIG. 1 with the outer skin layer removed and illustrating the perimeter edge extending tabs associated with the implant in individual engaging fashion with underlying muscle layer locations.

A plurality of perimeter edge spaced and underside engaging tabs further shown at 12, 14 and 16. Further illustrated in phantom at 18 is an underlying layer of muscle which is revealed by the removal of the skin. As further depicted in the plan view of FIG. 2, the implant in FIG. 1 with the outer skin layer again removed illustrates the perimeter edge extending tabs 12, 14, 16 associated with the implant in individual engaging fashion with underlying locations of the muscle layer 18. The use of the tabs 12, 14 and 16 allows the surgeon to secure and position the implant in a manner which maintains is orientation (angle) and prevents migration (movement) of the implant.

The breast implant 10, as further depicted throughout the succeeding embodiments, can include a bladder incorporating any type of synthetic plasticized, nylon, silicone or other suitable composite material which is filled with a suitably viscous or gelatinous material further including any type of silicone, saline or other mixture or admixture. The tabs 12, 14, 16 again shown in FIG. 2 each typically include a planar or supporting base component which is affixed or integrated into perimeter extending edge locations of the implant body 10.

An engaging portion extends from typically an outer location of the base supporting component (see as depicted by the flattened extending profiles of each of the tabs, 12, 14, and 16) and include a piercing or affixing portion extending therefrom which engages the muscle layer in order to affix the implant in place during the period in which the muscle and ligament structure sets. Alternate to puncturing or gripping the muscles, the tabs can be reconfigured such that the tab ends are sewn into the underlying muscle layer, it being understood that any pattern or number of clips or tabs are capable of being provided about a periphery of the implant. It is also understood that the tabs on the implant may be secured to the underlying fascia or muscle, in one non-limited application, with sutures.

Figure 3:
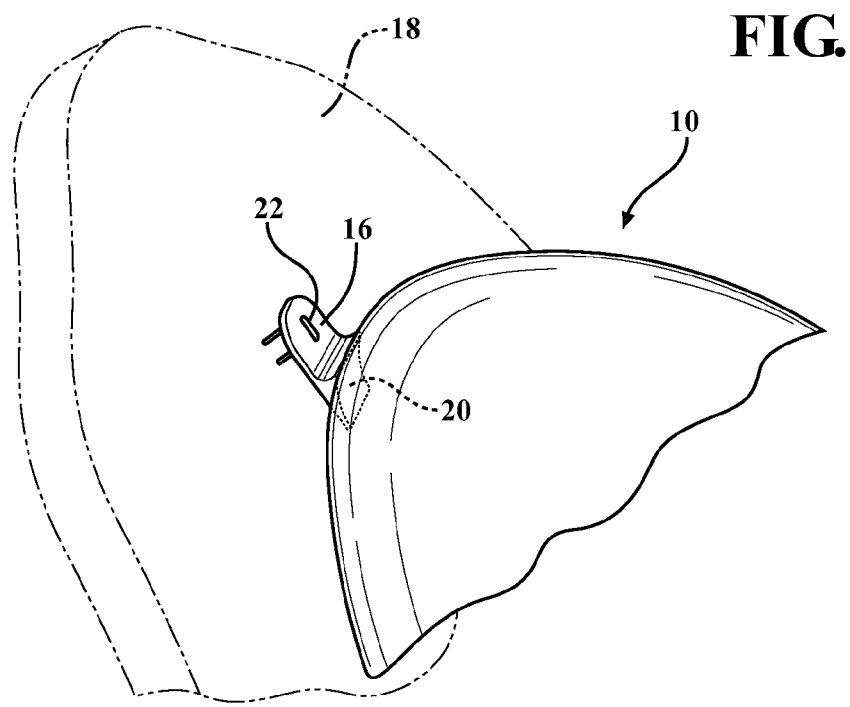
FIG. 3 is a further enlarged partial view depicting a selected tab sewn into an underlying muscle layer of the patient.

As further shown in FIG. 3, a further enlarged partial view depicts selected tab 16 according to one non-limiting configuration and which includes an arcuate shaped base portion 20 which is molded or otherwise adhered to a perimeter edge location of the breast implant 10. A staple 22 is further shown with a pair of extending prongs and which, in use, projects through an extending surface of the tab 16 and which is either punctured or sewn into the underlying muscle layer 18 of the patient. The oblique view provided better illustrates the nature in which the tabs are secured to the fascia/muscle through the use of sutures.

As will be described further, the present inventions contemplate a number of different styles and techniques for anchoring the tabs into the muscle layer 18. It is also envisioned and understood that any pattern or number of tabs or clips can be incorporated at specified locations around the implant.

Figure 4:
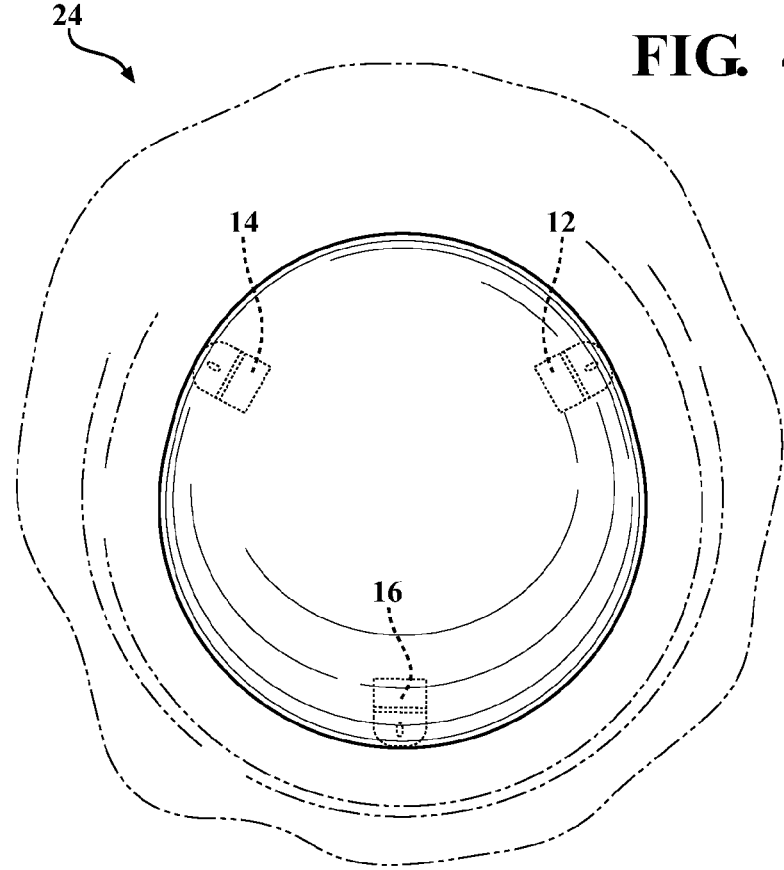
FIG. 4 is a plan view of a related variant in which the perimeter spaced tabs are reconfigured in a generally hidden fashion within the associated edge profile of the breast implant.

Referring further to FIG. 4, a plan view is depicted generally at 24 of a related variant in which the perimeter spaced tabs 12, 14 and 16 are reconfigured in a generally underside hidden fashion within the associated edge profile of the breast implant 10. The view of the sew-in tabs depicted in underneath fashion proximate the perimeter edge of the implant is again secured to the muscle/fascia through the use of a suture or other suitable connective medium.

Figure 5:
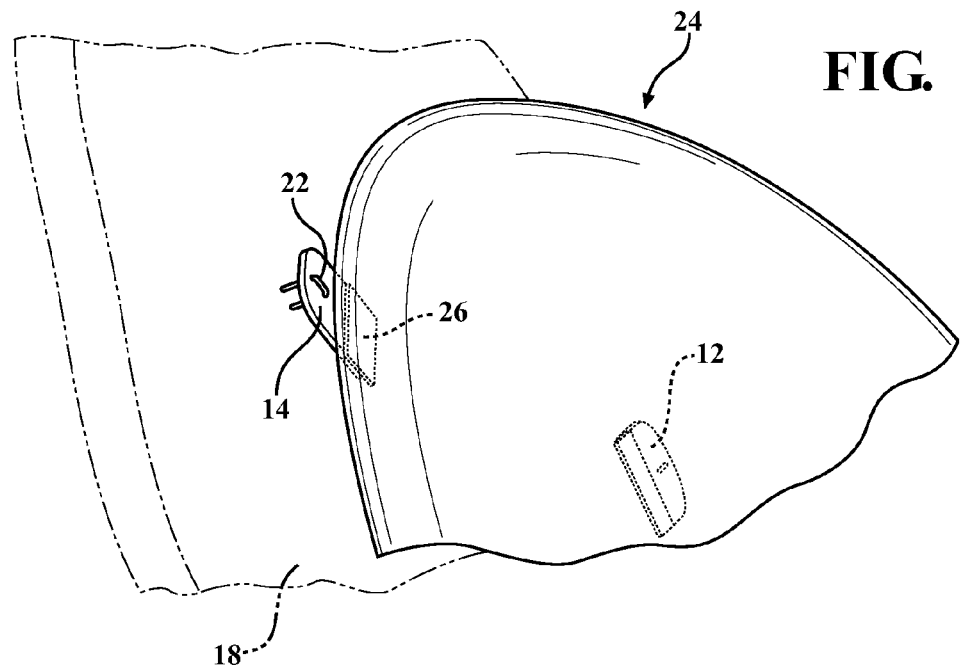
FIG. 5 is an enlarged view similar to that shown in FIG. 3 and depicting the tabs in FIG. 4 located underneath the edge perimeter of the implant and sewn in to the muscle layer.

FIG. 5 is an enlarged and oblique view similar to that shown in FIG. 3 and depicting the tabs in FIG. 4 repositioned underneath the edge perimeter of the implant and sewn in to the muscle layer of the chest through the use of sutures. The configuration of the tabs in this variant can further be such that the implant secured and extending base portion 20 depicted in FIG. 3 secured along a side to bottom proximate edge location is reconfigured in FIG. 5 as further shown at 26 to facilitate mounting to an underside edge proximate facing location of the implant bladder and thereby permit the tabs to be mounted to the muscle layer 18 in a substantially underside hidden fashion.

Figure 6:
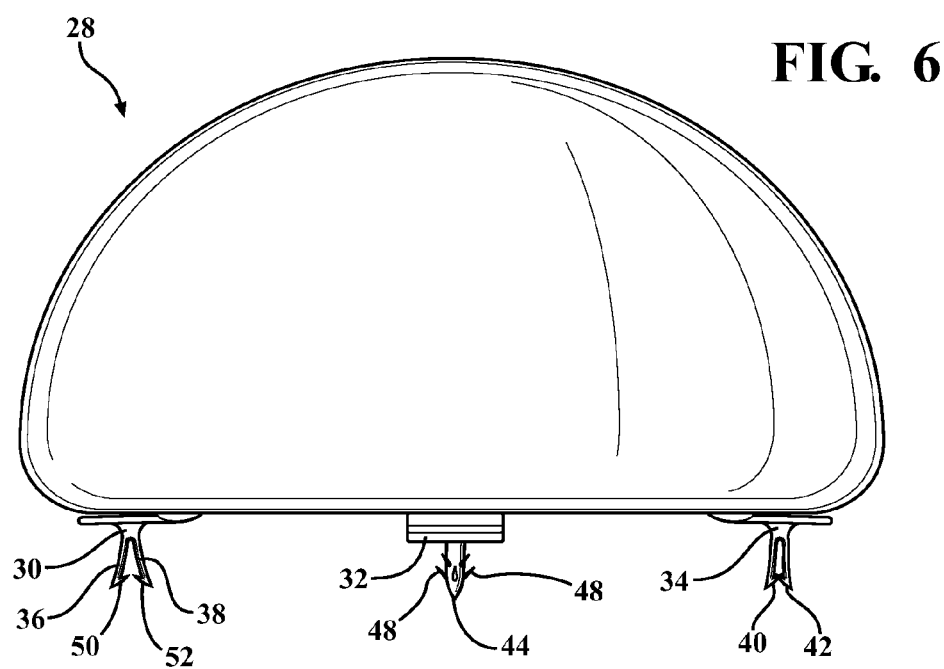
FIG. 6 is a side plan view of a similar implant design in which reconfigured and time-elapsed dissolvable mounting tabs are provided for engaging the underlying muscle layer.

Proceeding to FIG. 6, a side plan view is shown at 28 of a similar implant design in which alternately reconfigured tabs are respectively shown at 30, 32 and 34, each of the tabs (including the staples previously described) also contemplating being constructed of a material which is time-elapsed dissolvable. Each disclosed variant of the tabs is again provided with an associated base component similar in construction to that shown in FIG. 5 for engaging the underlying muscle layer. As depicted, the tabs can each exhibit any number of angled and deflectable tangs or barbs, these including such as shown at 36 and 38 for tab 30, as well as dual pairs of barbs 40 and 42 for tab 34.

The barbs can further exhibit reverse angled branches which assist in engaging (such as in a push-in fashion) the underlying muscle layer and such that the tabs can provide durable engagement of the breast implant to the muscle layer. As further disclosed, the material construction of the tabs, including such as a decay-able plastic or plastic composition, can be such that they are progressively dissolved over time and so that eventual disappearance of the tabs (defined as including both the base affixing components and the associated prongs/barbs/staples) can coincide with the emergence of natural engaging muscle and tissue enveloping the implant and such that no follow up procedures are required in order to remove the staples.

Figure 7:
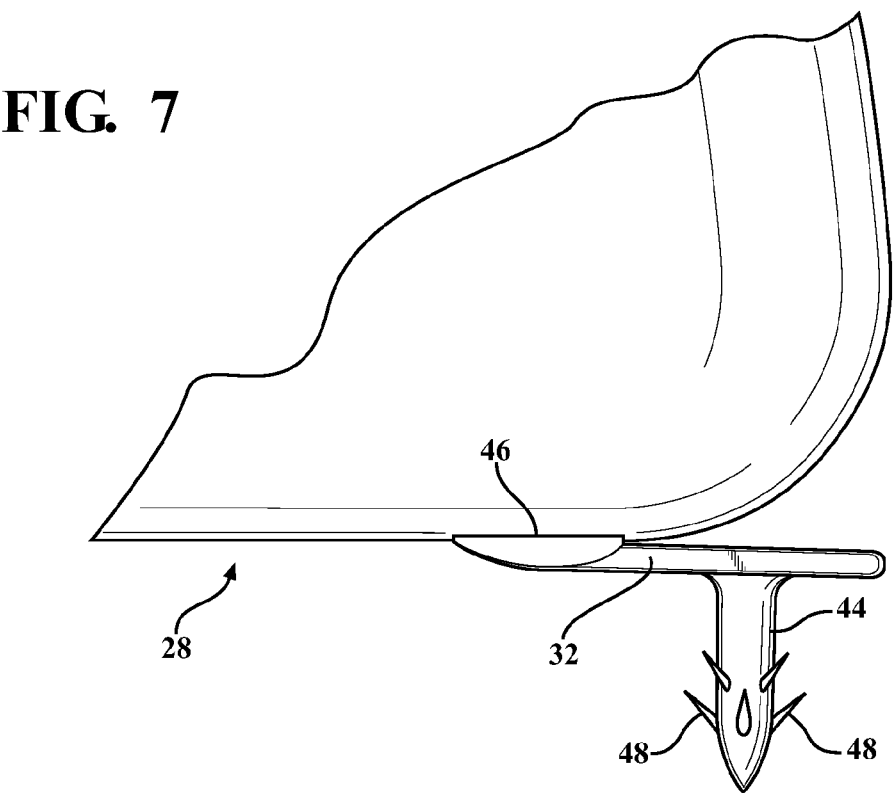
FIG. 7 is an enlarged side view of an implant incorporating a further tab design and illustrating the configuration of the underlying and implant mounting support for protecting the implant from the inwardly barbed points associated with the projecting post.

Further depicted at tab 32 is a single enlarged stem shaped post 44 (see also shown in FIG. 7). The further tab design is illustrated as having the configuration of an underlying and implant mounting support base, at 46, for protecting the implant body 28 from reverse angled barbs 48 of the implant associated with the projecting post. The implant 28 is protected from the "spine like" barb portions 48 via the tab 32 previously described, and is pressed installed into the underlying muscle layer and, at least initially, held in place by the reverse angled barbed features 48, these likewise exhibiting a time progressive dissolving composition corresponding to natural muscle and connective ligament growth for securing the implant to the inner muscle layer.

Figure 8:
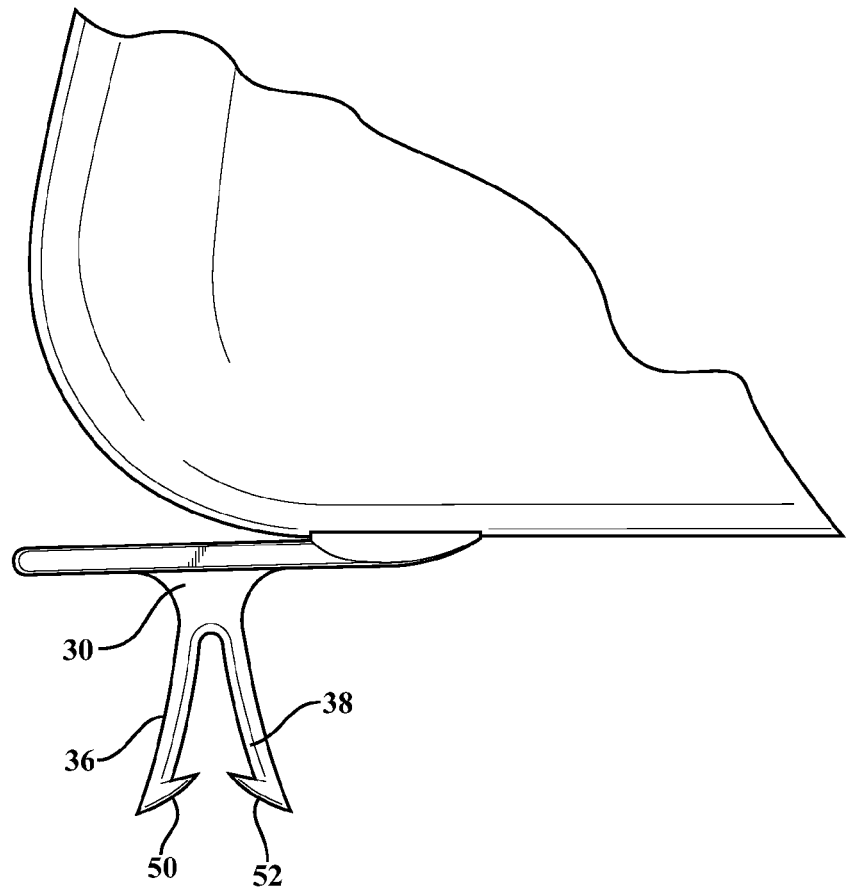
FIG. 8 is an enlarged side view of a further barbed tab design secured to an underside perimeter location of a breast implant and which is pushed into and grippingly engaged to the underlying muscle layer.

FIG. 8 is an enlarged side view of a further barbed tab design, such as previously depicted at 30 in FIG. 6 with angled tangs 36 and 38, as well as inwardly end angled barbs 50 and 52, secured to an underside perimeter location of breast implant 28 and which is pushed into and grippingly engaged to the underlying muscle layer. The configuration of the tab 30 is further such that the barbs and supporting tangs are constructed of a material sufficient resilient and biasing (as well as optionally time dissolvable) and facilitate engagement upon being pushed into the muscle layer and further by virtue of spreading and gripping of the opposing barbs onto the muscle. Again, the tab can either be constructed as a time elapse dissolvable component or can be provided as a durable construction.

Figure 9:
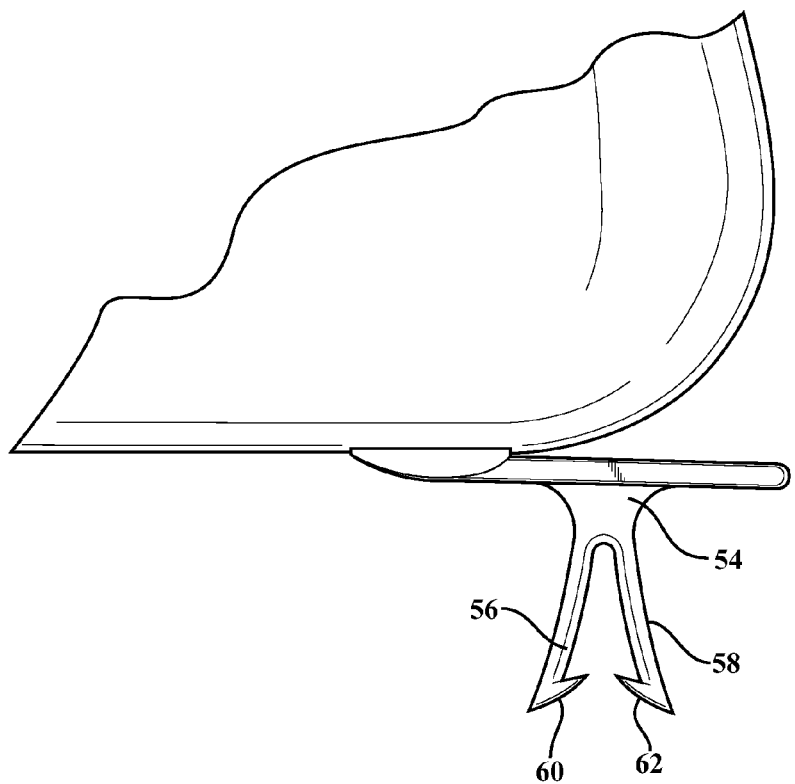
FIG. 9 is an opposite end view of another tab similar to that shown in FIG. 8 and exhibiting a crimped barb design which is adapted to being pushed into the underlying muscle and which is time-elapsed dissolvable to permit the implant adequate time to naturally anchor in location.
Figure 10:
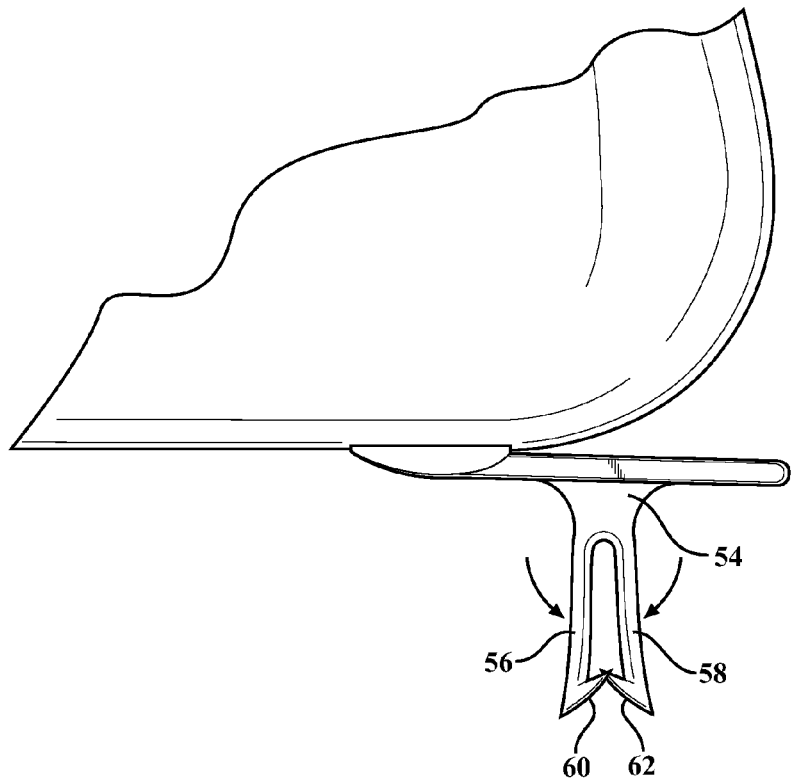
FIG. 10 is a succeeding illustration to FIG. 9 and in which the barbs are closed together in order to grip to a proximate muscle location.

FIG. 9 is an opposite end view of another tab, identified at 54, which is similar to that shown in FIG. 8 and exhibiting a likewise crimped barb design which is adapted to being pushed into the underlying muscle and which is time-elapsed dissolvable to permit the implant adequate time to naturally anchor in location. FIG. 10 is a succeeding illustration of the muscle engaging tab 54 in FIG. 9, and in which associated tangs 56 and 58 with inwardly angled barbs 60 and 62 are inwardly pivoted/closed together (such as through the application of a crimping tool) at the time of implantation in the manner depicted and in order that the barbs grip therebetween a proximate muscle location (not shown). As described, the tab can again be dissolvable over time if desired.

Figure 11:
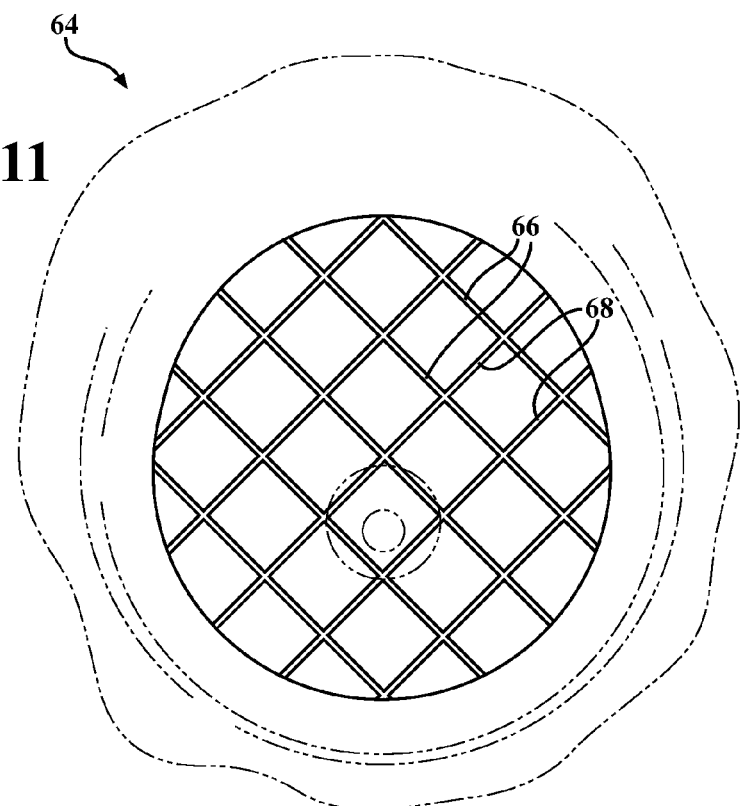
FIG. 11 is a plan view of a further variant of breast implant and which incorporates a plurality of interior partitions or chambers exhibiting any shape or design including diagonal as shown, and which are either or both individually arrayed or vented/interconnected, and which can be filled with any type of silicone, saline or combination of fluid.

Having described in detail non-limiting examples of alternately configured tabs and like muscle engaging portions, and now proceeding to FIG. 11, a plan view is shown at 64 of a further variant of breast implant which is emplaced at the time of breast reconstruction or augmentation. The implant 64 incorporates a plurality of interior partitions or chambers, see interconnecting walls 66, 68, et seq. arranged in a generally two dimensional grid shape. Beyond that depicted, the grid arrangement can exhibit any shape or design not limited to the generally diagonal arrangement as shown, and which are either or both individually arrayed/isolated or vented/interconnected (or established with some combination of isolated and inter-vented chambers), and which can be filled with any type of silicone, saline or combination of fluid. As will be described throughout the succeeding illustrations, the implant chambers can be filled with any form of gelatinous or viscous material not limited to silicone/saline or any combination thereof.

As will be further described with reference throughout the succeeding embodiments, the arrangement of the chambers or sub-enclosures can be modified or varied between the individual chambers. Also subsequently described will be the provision of any type of venting or apertures established between the individual chambers and which enable controlled fluid sharing/flow between the chambers to provide the implant with additional properties which further mimic that of natural breast tissue.

Figure 12:
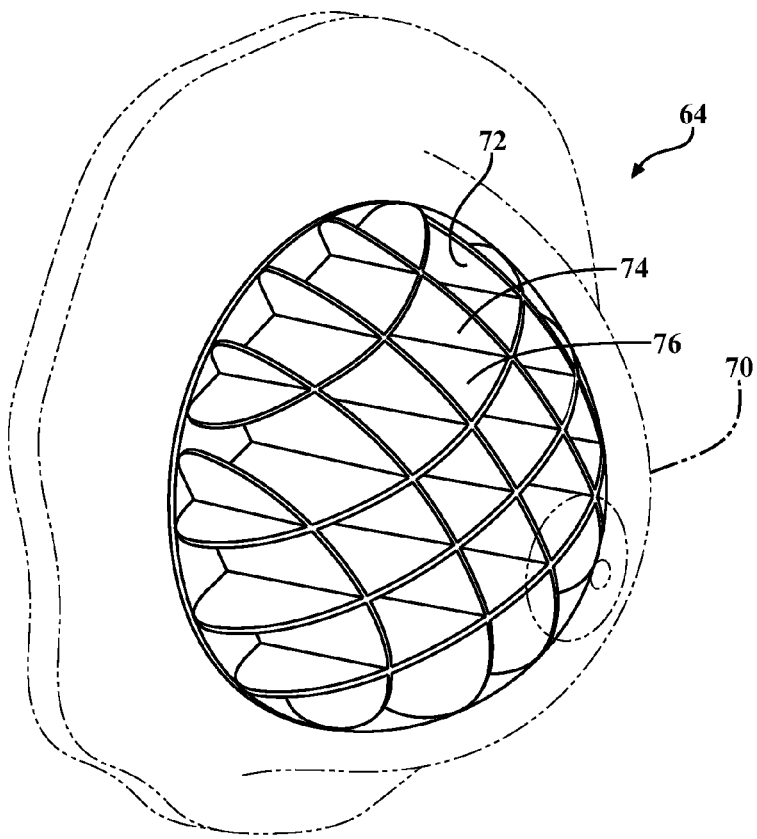
FIG. 12 is a rotated perspective view of the implant depicted in FIG. 11, exhibiting the exterior skin layer in partially transparent fashion, and better illustrating the selected three dimensional diagonal shape of the individual chamber partitions.

FIG. 12 is a rotated perspective view of the implant 64 depicted in FIG. 11 and exhibiting exterior skin layer 70 in partially transparent fashion. The perspective shown the implant 64 better illustrates the three dimensional diagonal shape of the plurality of individual and arcuate outer edge configured chamber partitions 72, 74, 76, et seq. which are created by the various series of interconnected walls (again as previously depicted at 66, 68, et seq. in two dimension in FIG. 11). As previously indicated, the plasticized or silicone based construction of the implant bladder can be filled with any suitable gelatinous or viscous fluidic material including again any type of liquid silicone, saline based solution or the like.

Figure 13:
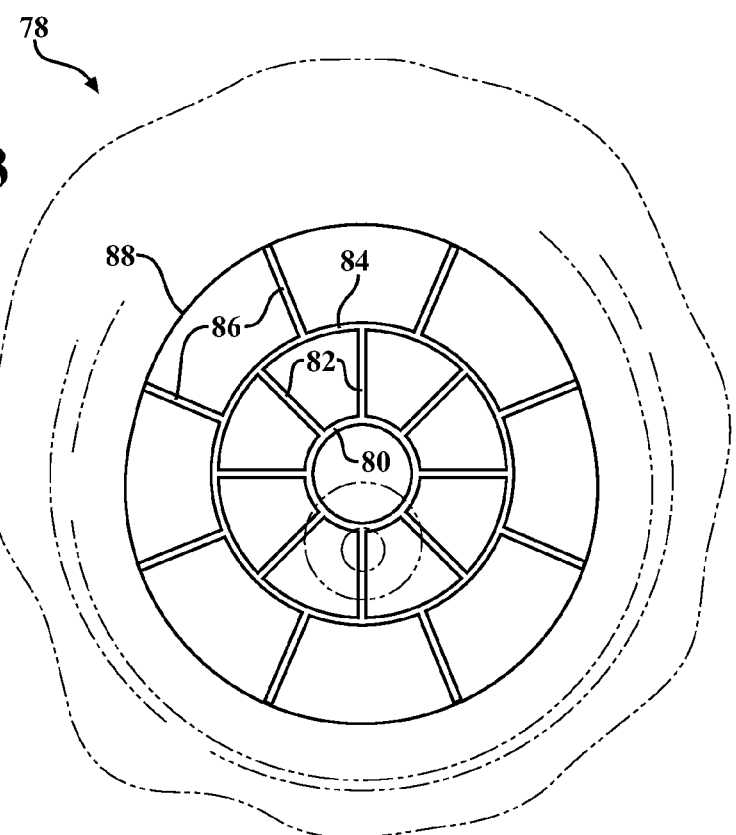
FIG. 13 is an end plan view similar to FIG. 11 and of a further modified circular/sectioned chamber design.
Figure 14:
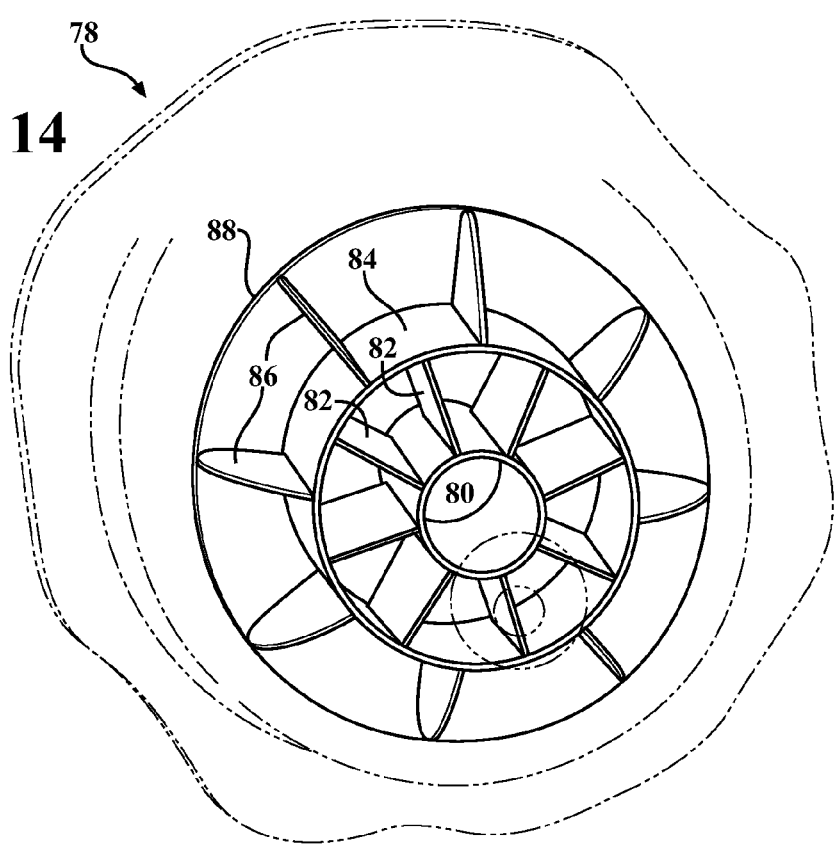
FIG. 14 is a rotated perspective view of the design in FIG. 13.

FIG. 13 is an end plan view 78 similar to FIG. 11 and of a further modified circular/sectioned chamber design integrated into a generally dome shaped and three dimensional breast implant. FIG. 14 is a rotated perspective view of the design in FIG. 13 and better depicting, in three dimension, the configuration of chamber defining partitions including central circular wall 80, spoke extending walls 82 extending to intermediate circular wall 84, and further outer spoke extending walls 86 extending to outermost circular perimeter defining wall 88.

Figure 15:
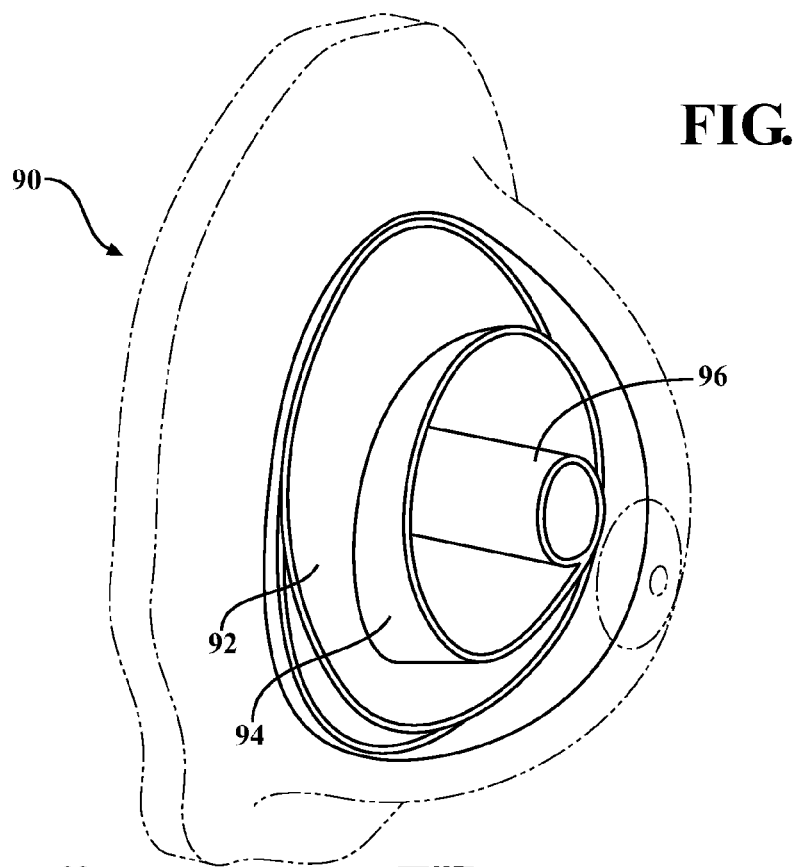
FIG. 15 is perspective view of a further implant design exhibiting a spiral chamber configuration.
Figure 16:
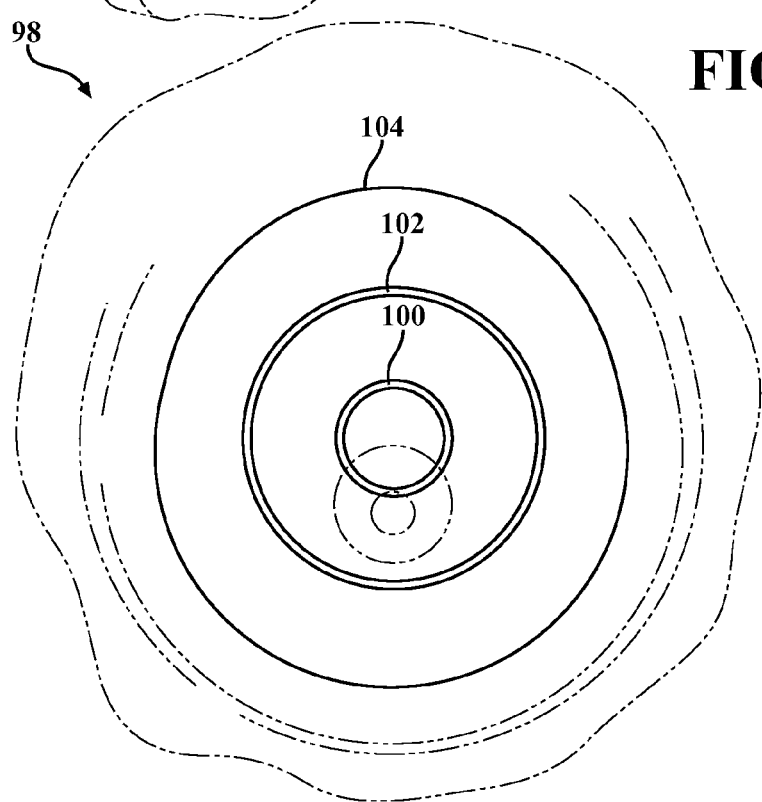
FIG. 16 is a further plan view of a radial chamber design incorporated into a further variant of breast implant.

FIG. 15 is perspective view in partial cutaway, at 90, of a further implant design exhibiting a radial/sliced (or spiral) chamber configuration as further depicted by overlapping and spiral arranged walls 92, 94, et seq. extending about a central stem partition 96. FIG. 16 is a further plan view generally at 98 of a radial chamber design incorporated into a further variant of breast implant and including concentric arranged partition chamber defining walls 100, 102, 104.

Figure 17:
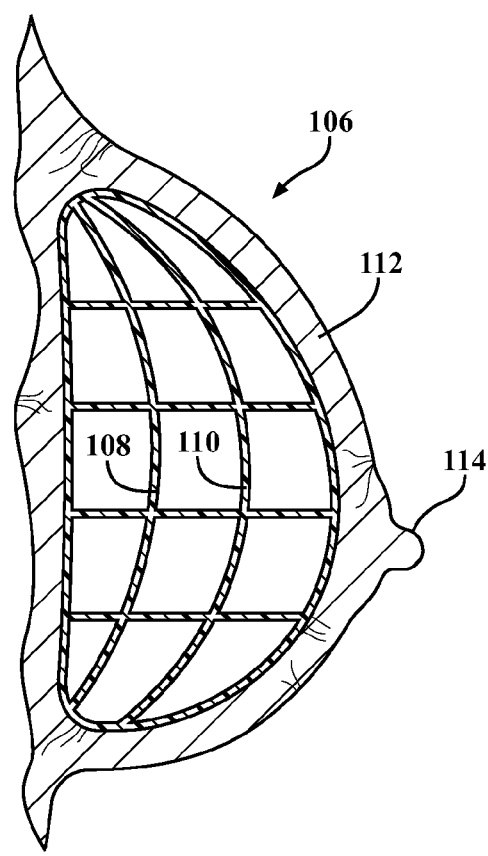
FIG. 17 a side cutaway environmental view of a further variant of breast implant and depicting arcuate shaped and internally extending membrane supports.

FIG. 17 a side cutaway environmental view 106 of a further variant of breast implant and depicting arcuate shaped and internally extending membrane supports 108 and 110 incorporated into the implant body which is in turn illustrated supported within a tissue/skin overlay 112. Also shown at 114 is an environmental depiction of a nipple implant which, as will be described subsequently in more detail, can either remain as part of an initial breast construction or alternately can include a separate or combination implant construction. Consistent also with the descriptions previously provided, the individual defined chambers can exhibit any design or shape, including polygonal, arcuate or otherwise, and with or without venting or other inter-chamber fluid communication in order to modify the viscous holding and fluidic transfer properties of the interiorly held fluid medium.

Figure 18:
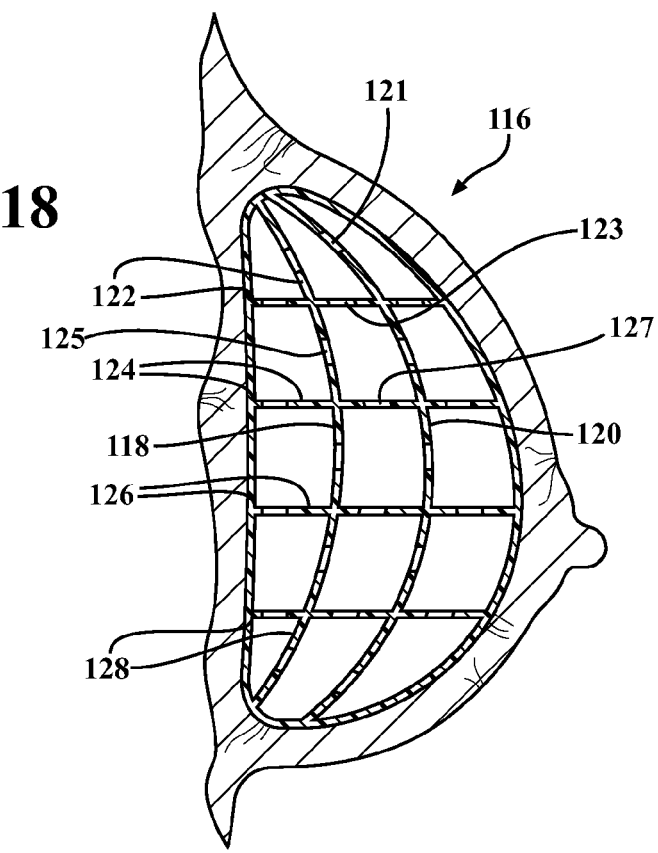
FIG. 18 is a further side cutaway of another version of multi-tiered and internal vented support configuration associated with a breast implant and in which the vents are located in centered fashion relative to each chamber.
Figure 19:
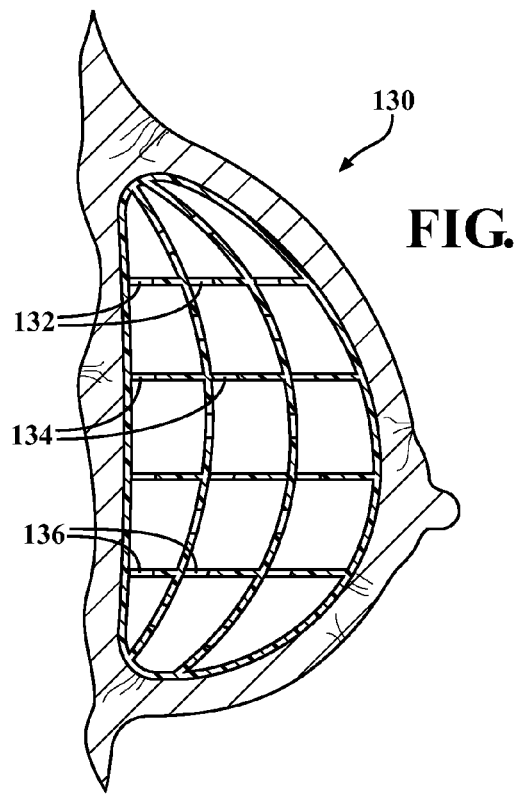
FIG. 19 is an illustration similar to FIG. 18 and in which the vents are repositioned inboard of each chamber.

FIG. 18 is a further side cutaway of another version 116 of multi-tiered and internal vented support configuration associated with a breast implant, see again arcuate and internally extending, as well as segmented, membrane supports 118 and 120, which are interconnected with generally crosswise perpendicular segmented walls 122, 124, 126, and 128, and in which a plurality of vents (see as shown by communicating apertures 121, 123, 125, 127) located in centered or any offset fashion relative to each individual chamber defining inner wall. FIG. 19 is an illustration similar to FIG. 18 of a related variant 130 and in which the crosswise extending vents are repositioned inboard of each chamber as further depicted by gaps 132, 134, 136, et seq., such as in combination with the specified material construction of the inner sub chamber defining walls further modifying the physical properties of the implant interior to further mimic that of natural breast tissue.

Figure 20:
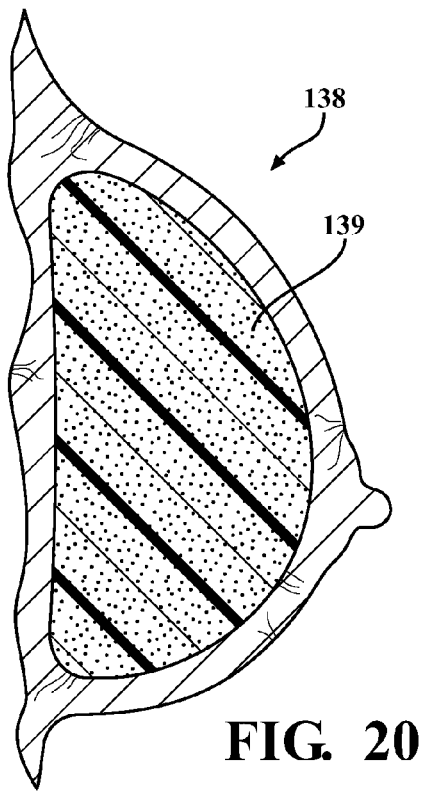
FIG. 20 is an illustration of a sponge implant configuration which can incorporate any combination of sponge, silicone, and/or saline components.
Figure 21:
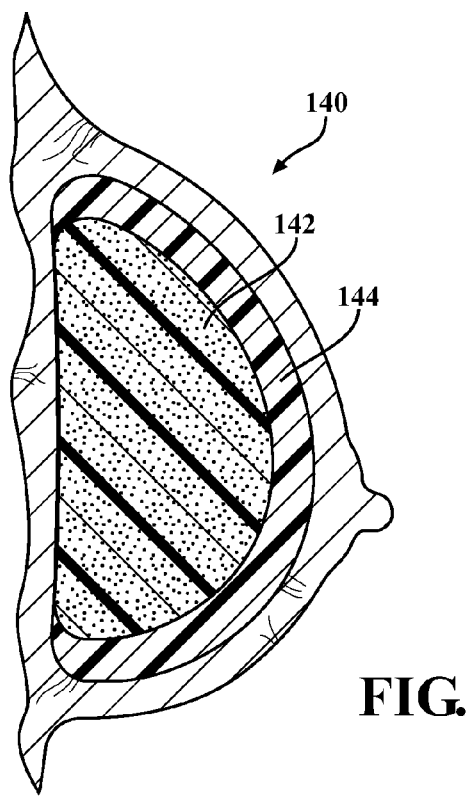
FIG. 21 is an illustration of a modified design to that shown in FIG. 20 and in which an inner sponge is surrounded by an outer layer of thickened silicone/saline.

Referring to FIG. 20, an illustration is depicted generally at 138 of a sponge implant 139 configuration which can incorporate any combination of sponge, silicone, and/or saline components according to any arrangement of internally held or entrained fluidic medium. FIG. 21 is a modified design illustration 140 of a variant to that shown in FIG. 20 and in which illustrates in cutaway an inner sponge 142 is surrounded by an outer layer of thickened silicone/saline 144.

Figure 22:
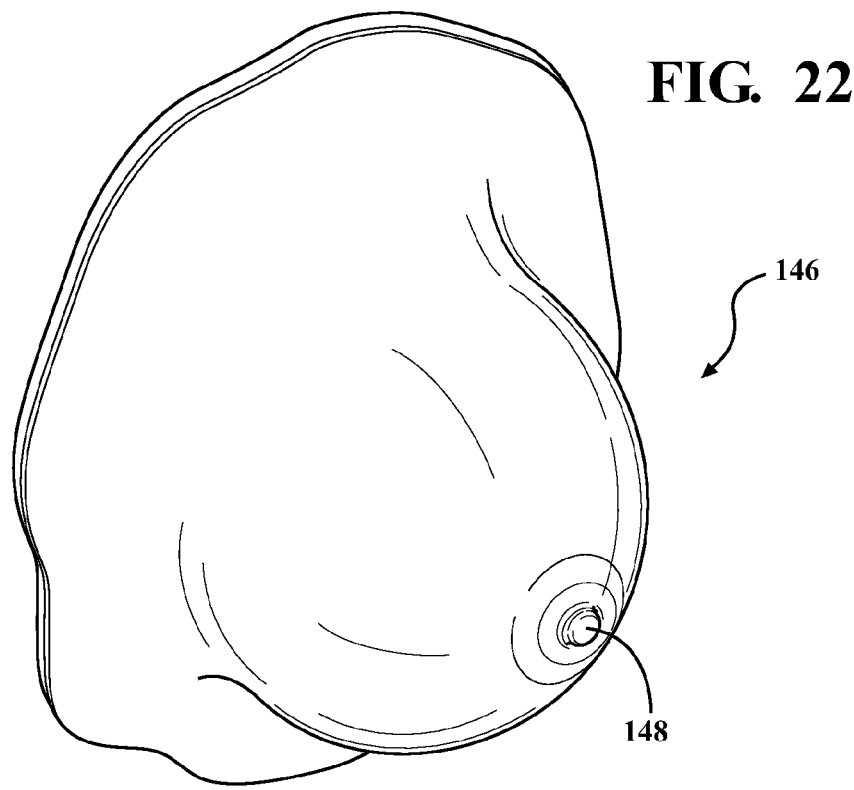
FIG. 22 is a first environmental perspective view of a combination of breast and nipple implants, and in which the nipple implant is depicted in a first relaxed (i.e. non-arousal) position.
Figure 23:
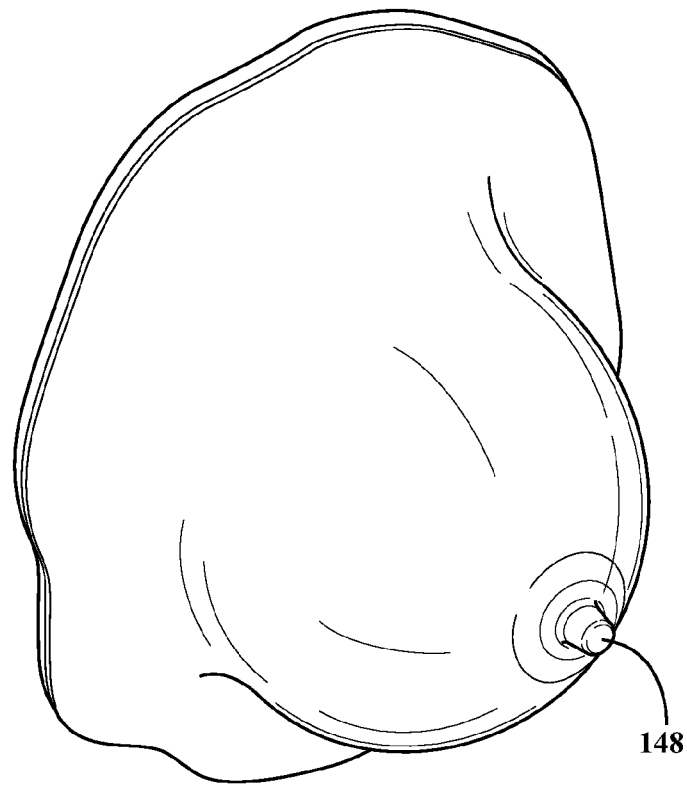
FIG. 23 is a succeeding illustration depicting the nipple implant in an expanded (i.e. arousal) position which mimics the sexual arousal response of natural tissue.

FIG. 22 is a first exterior environmental perspective view 146 of a combination of installed breast and nipple implants (not shown), and in which a centrally positioned and outermost located nipple implant (defined by outermost projecting nipple 148) is depicted in a first relaxed position. FIG. 23 is a succeeding illustration depicting the nipple implant in an expanded position, again at 148, and which can be designed to mimic auto-arousal sexual responses which are typically associated with natural tissue.

Figure 24:
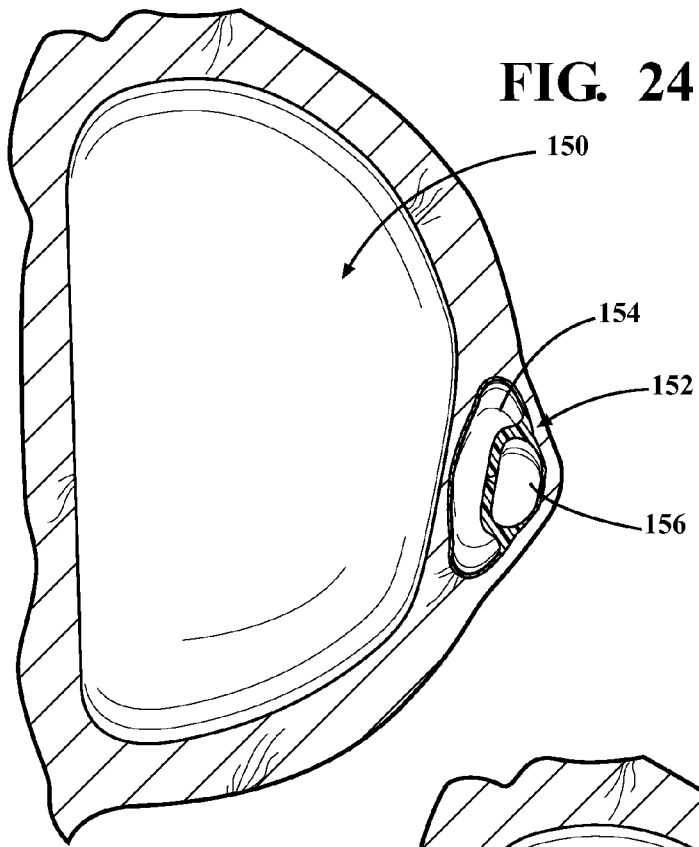
FIG. 24 is a side view illustration of dedicated breast and nipple implants in the position of FIG. 22 and illustrating the outer tissue/skin and underlying muscle layer in partial phantom.

FIG. 24 is a side view illustration of dedicated breast 150 and nipple 152 implants in the position of FIG. 22 and depicted in side cutaway. The implants are inserted at the time of reconstruction or augmentation and it is further envisioned that the nipple extender can be emplaced at the same time as the breast implant or installed individually in a patient who has had an autogenous breast/implant reconstruction procedure.

Figure 25:
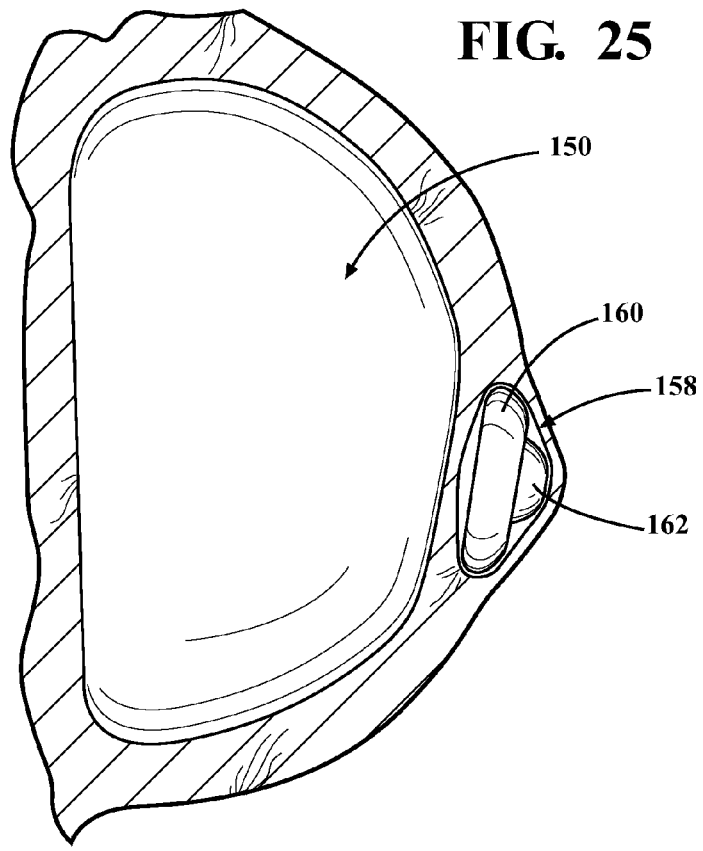
FIG. 25 is a succeeding illustration depicting an annular shaped sponge reservoir chamber for supplying pressurized fluid to a centrally positioned and extendable/retractable nipple chamber.

As further shown in FIG. 25, which is a succeeding illustration, additional depicted features of the nipple implant 152 include the provision of an annular shaped reservoir chamber 154 (exhibiting a pseudo doughnut shape) for supplying an internally held pressurized fluid (not limited to any of these previously described in relation to the underlying breast implant) to a centrally positioned, fluidly/valve communicating and extendable/retractable nipple chamber 156. The nipple extenders shown are emplaced in any of subcutaneous, sub-glandular or sub-muscular fashion. As will be depicted in further embodiments, a variety of differing types of flow, check and gate valves can be employed for permitting physical manipulation of the annular reservoir chamber 154 to cause inflation of the central extendable nipple chamber 156. The breast implant, again generally depicted at 150, is considered similar to the constructions previously noted, unless otherwise indicated.

Figure 26:
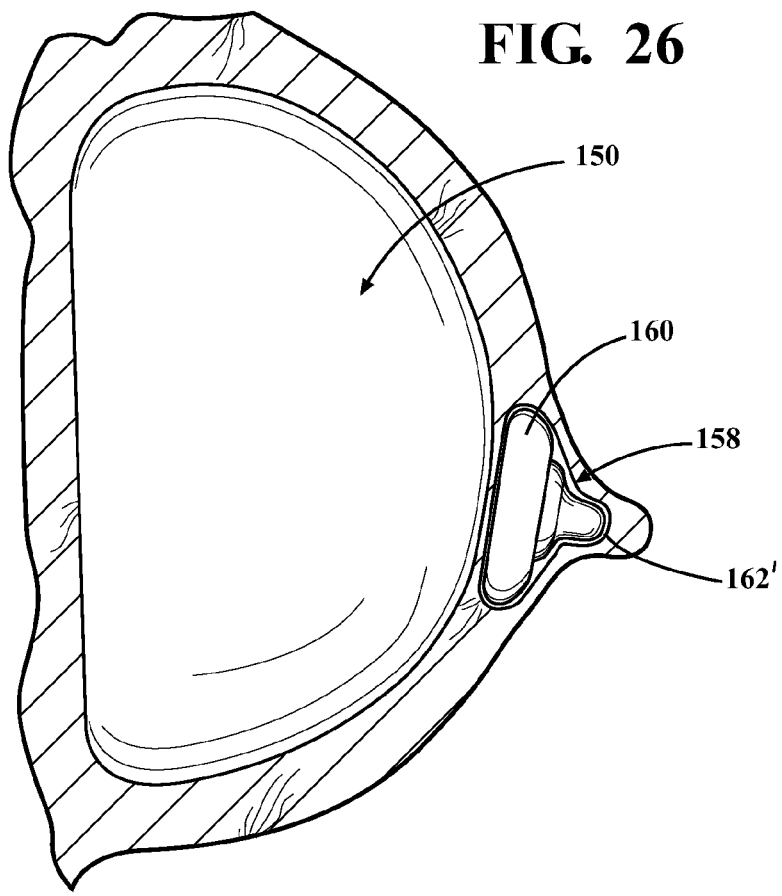
FIG. 26 is a succeeding illustration to that shown of FIG. 25 of the nipple chamber influenced to an extended position consistent with mimicking arousal properties normally associated with blood flow to natural nipple tissue.

FIG. 25 is an illustration depicting a variation of the nipple implant 158 incorporating an annular shaped sponge reservoir chamber 160 (similar to that depicted at 154 in FIG. 24) and for supplying pressurized fluid to a centrally positioned and extendable/retractable nipple chamber 162 (likewise similar to that shown at 156 in FIG. 24). FIG. 26 is a succeeding illustration of the reservoir nipple chamber in FIG. 25 in a projecting or extended position, see at 162', again as a result of physical manipulation of the annular reservoir chamber 160 and consistent with mimicking arousal properties normally associated with blood flow to natural nipple tissue.

Figure 27:
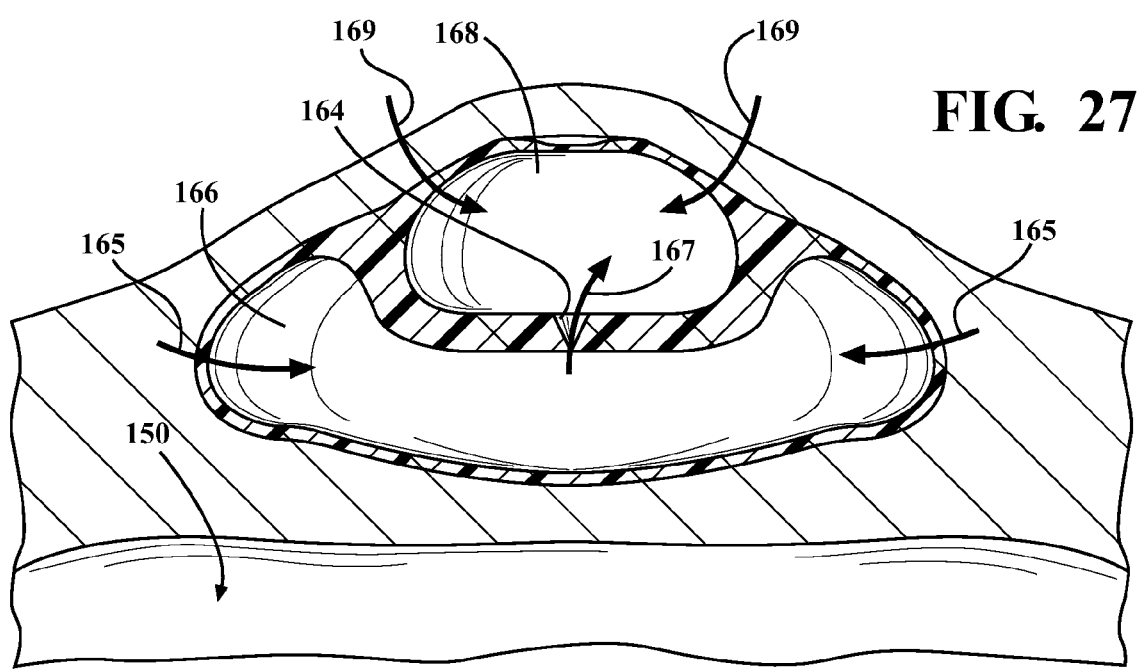
FIG. 27 is an enlarged side view of the nipple implant and illustrating a valve passageway established between the reservoir and nipple chambers.
Figure 28:
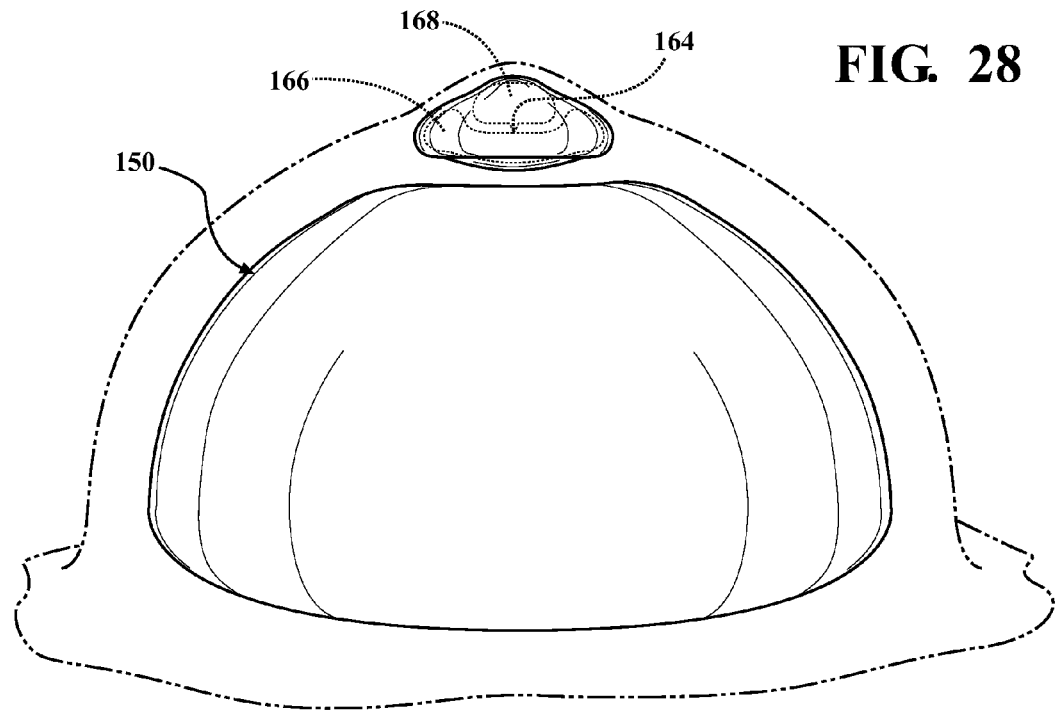
FIG. 28 is a succeeding illustration of a fluid transfer arrangement established between the reservoir and nipple chambers and by which a first squeezing application to the annular shaped reservoir chamber causes fluid flow within the nipple chamber, with consequent depressing of the nipple chamber returning fluid under pressure to the interconnected reservoir chamber via a flow valve established therebetween.

Proceeding to FIG. 27, an enlarged side view is depicted of a nipple implant and illustrating, at 164 a valve passageway established between communicating outer reservoir 166 and nipple (relaxed) 168 chambers. FIG. 28 is a succeeding illustration of a fluid transfer arrangement established between the reservoir 166 and nipple (extended) 168 chambers and by which a first squeezing application (see directional arrows 165 in enlarged FIG. 27) to the annular shaped reservoir chamber 166 causes fluid flow through the valve 164 (via further directional arrows 167), within the nipple chamber 168, with consequent depressing of the nipple chamber (via arrows 169 extending in an inward pinching direction) returning fluid under pressure to the interconnected reservoir chamber via a flow valve established therebetween and in order to return retract the nipple chamber 168 to the position originally depicted in FIG. 27.

Figure 29:
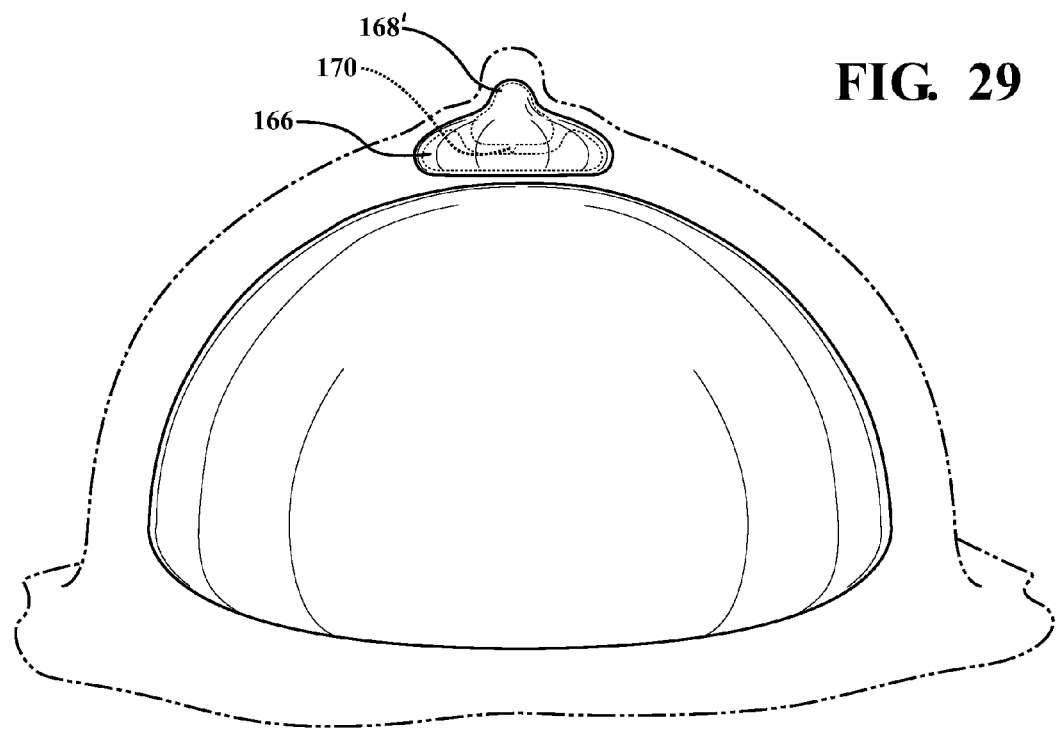
FIG. 29 is a succeeding illustration in which an initial expansion of the nipple chamber is maintained by such as a check valve configured in the passageway established between the reservoir and nipple chambers, the configuration also contemplating a slow return leak of fluid from the nipple to the reservoir chamber, thereby causing a slow collapse of the nipple.

FIG. 29 is a succeeding illustration in which an initial expansion of the nipple chamber, see at 168', is maintained by such as a check valve (as depicted at 170) configured in the passageway established between the reservoir 166 and nipple 168 chambers. Following the inflation, the nipple chamber 168 can be pressed or squeezed (see again as depicted by directional arrows 169 in FIG. 27) to thereby overpower the pressure exerted on the inlet side of the check valve 170 and in order to transfer fluid back to the reservoir chamber 166. The configuration also contemplates a slow return leak of fluid from the nipple chamber 168 to the reservoir chamber 166, thereby causing a slow collapse of the nipple, such as which can be designed over a period of minutes.

Figure 30:
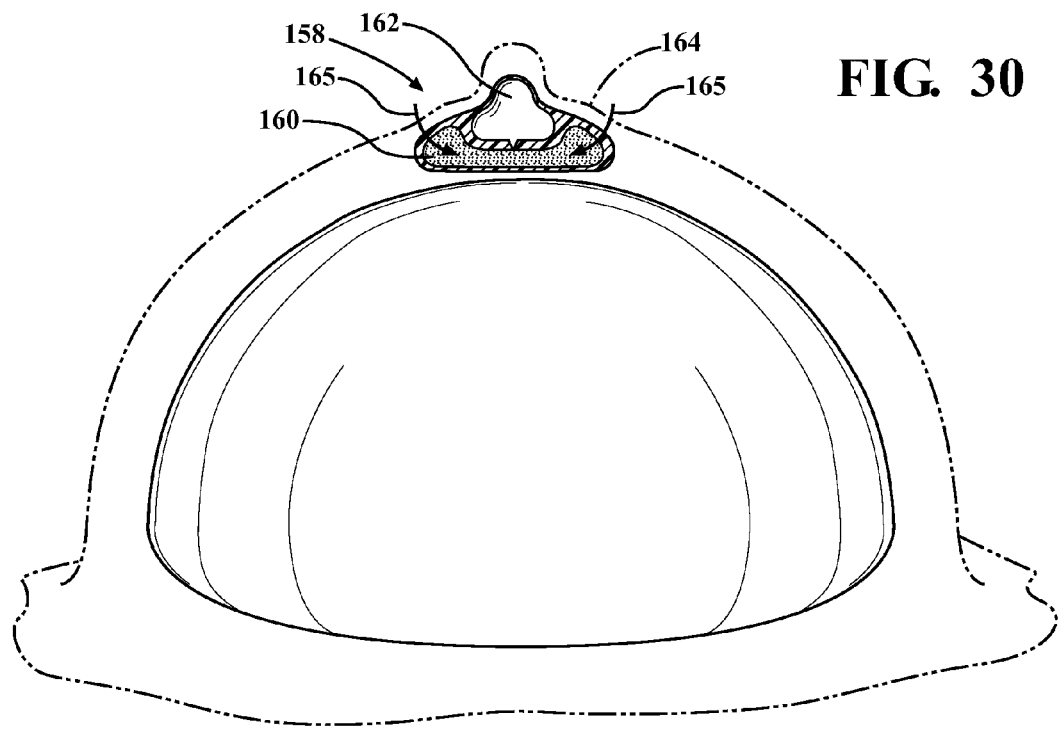
FIG. 30 is an illustrative depiction of a sponge reservoir chamber in communication with the central and extendable nipple chamber and which is operative in a similar fashion as described.

FIG. 30 is an illustrative depiction, in a partial side cutaway, of a sponge reservoir chamber, such as previously depicted at 160 associated with similar nipple implant 158 in FIGS. 25 and 26, in communication with the central and extendable nipple chamber 162 and which is operative in a similar fashion as described in FIG. 29 and which can be constructed of any elastic and resilient material which is designed to withstand repeated expansion/collapsing cycles. This can also include the steps of pressing or squeezing the surrounding areola (see directional arrows 165 as also shown in FIG. 27) depicted in the outer skin layer (at 164) in order to open the intercommunicating valve (not shown) and to cause fluid held within the chamber sponge 160 to flow into and extend the nipple chamber 162.

Without limitation, any variation of annular reservoir, whether silicone/plastic or sponge filled and plasticized encased according to any depiction shown herein can hold pneumatic fluid (air) or liquid fluid (water) under either ambient or increased pressure. It is further envisioned in further sub-variants that the user can manipulate the reservoir in any desired fashion to increase pressure either within the annular reservoir or either to/from the annular reservoir and nipple extending chamber reservoir by further virtue of the selected valve configured therebetween.

Figure 31:
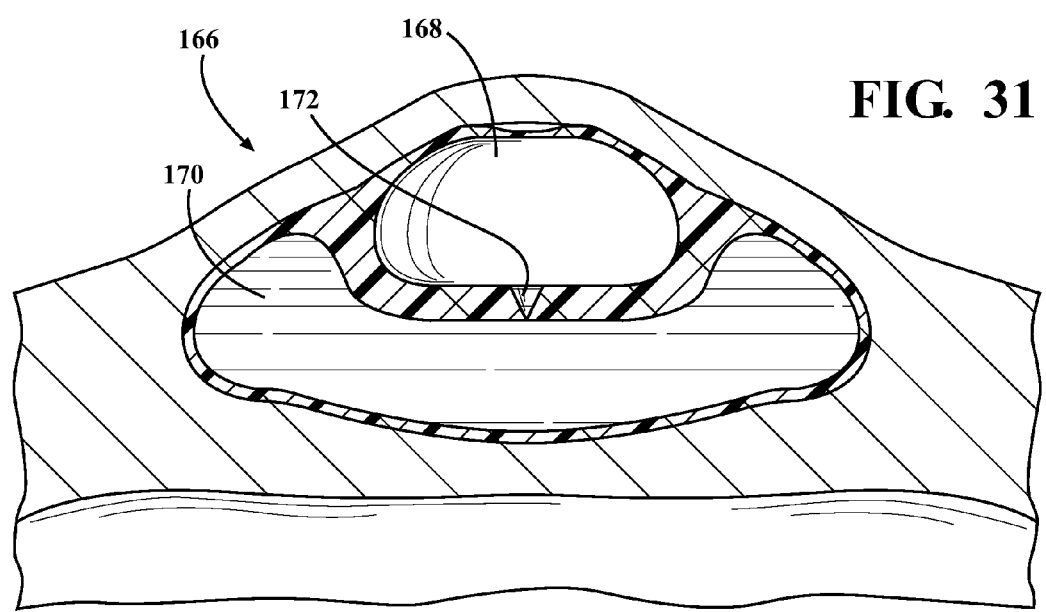
FIG. 31 is an illustration of a pressurized nipple configuration and in which the reservoir chamber is pressurized with fluid as an alternative to an ambient pressure fluid which is manually pumped by the user between nipple chamber extended and relaxed positions.

Accordingly, and proceeding to FIG. 31, an illustration is shown at 166 of a pressurized nipple configuration and in which the reservoir chamber is pressurized with fluid as an alternative to holding an ambient pressure of fluid and which is manually pumped by the user between nipple chamber extended and relaxed positions. In this variant, extender chamber 168 is collapsed with a minimal amount fluid passing to the annular reservoir chamber 170 via interconnecting valve 172.

Figure 32:
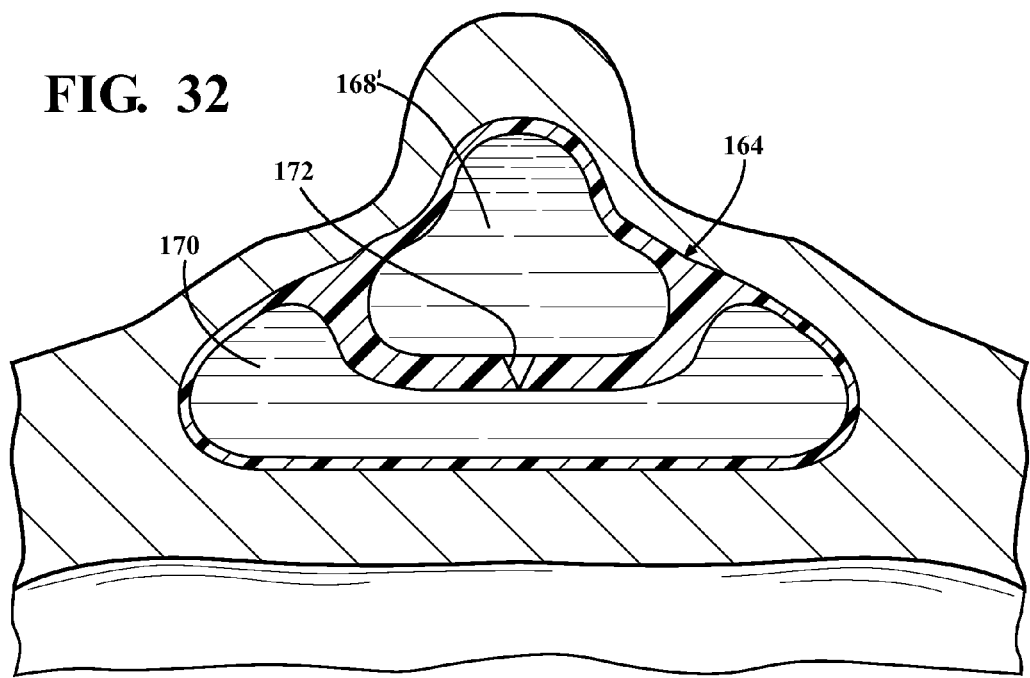
FIG. 32 is a succeeding illustration to FIG. 31 and in which depressing of the areola causes fluid to flow through a stop valve from the reservoir chamber to the nipple chamber for extending the nipple, following which upon the nipple chamber being firmly squeezed, fluid pressure within the reservoir chamber is overpowered and an interconnected a first stop valve is causes to allow fluid to transfer from the nipple back into the reservoir, following which release causes a separate check valve to retain the fluid within the reservoir.

FIG. 32 is a succeeding illustration to FIG. 31 and in which depressing of the areola, again at 164, causes fluid to flow through a stop valve, again at 172, from reservoir chamber 170 to the nipple chamber for extending the nipple (at 168' denoting the expanded position as opposed to substantially collapsed at 168 in FIG. 31). Following this, and upon the nipple chamber being firmly squeezed, fluid pressure within the reservoir chamber is overpowered and the stop valve 172 is causes to allow fluid to transfer from the nipple back into the reservoir, following which release causes a separate check valve (not shown) to retain the fluid within the reservoir and thereby the nipple extending chamber in the relaxed position (again FIG. 31).

Figure 33:
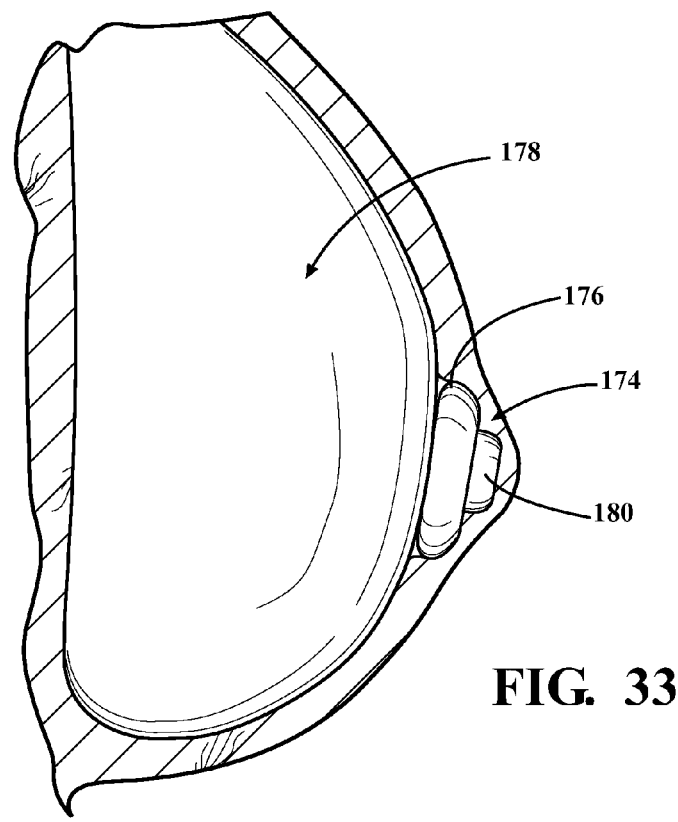
FIG. 33 an illustration of a succeeding embodiment in which a relaxed nipple implant is attached to a surface of the underlying breast implant.
Figure 34:
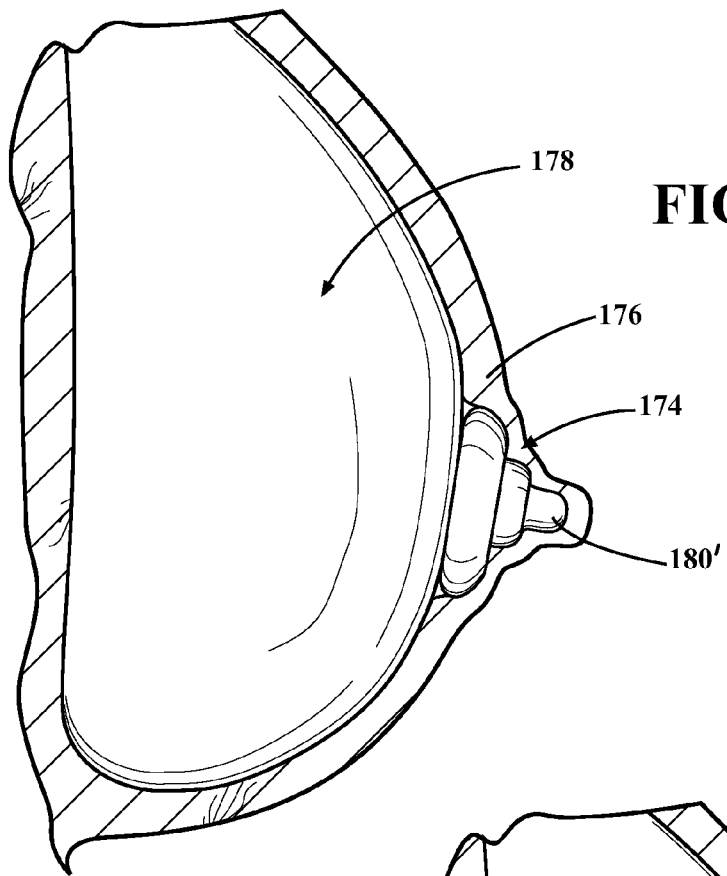
FIG. 34 is a succeeding illustration of an expanded nipple implant in the variant o FIG. 33.

FIG. 33 an illustration of a succeeding embodiment generally at 174 in which a relaxed nipple implant 176 is attached to a surface of the underlying breast implant 178. FIG. 34 is a succeeding illustration of an expanded nipple implant in the variant of FIG. 33 and by which a central nipple chamber expands from a relaxed position, at 180 in FIG. 33, to an extended position at 180' in FIG. 34.

Figure 35:
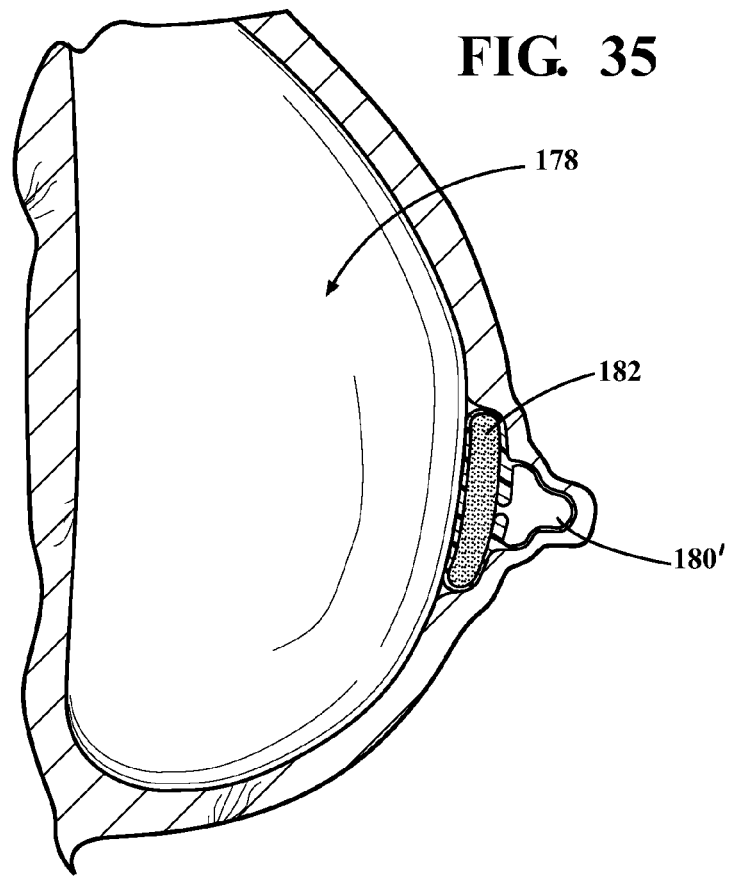
FIG. 35 is an illustration of a sponge reservoir for providing pressurized fluid to a nipple extender chamber.
Figure 36:
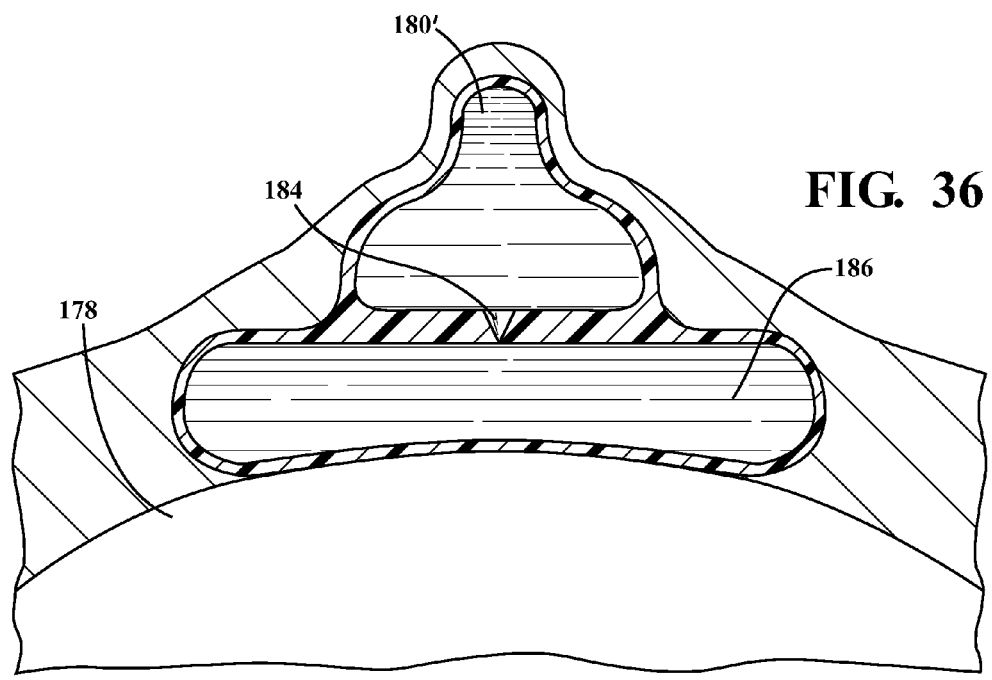
FIG. 36 is an enlarged side view better showing a valve passageway established between the nipple extender chamber and underlying reservoir chamber.

FIG. 35 is an illustration of an alternate variant of nipple implant similar to that depicted in FIG. 33, with the exception of a sponge reservoir 182 for providing pressurized fluid to a nipple extender chamber, again shown at 180' to denote its expanded position. FIG. 36 is an enlarged side view better showing a valve passageway 184 established between the nipple extender chamber (again at 180') and an underlying reservoir chamber, further shown at 186. The reservoir chamber 186 is shown attached to the surface of the underlying breast implant 178 and, as will be further described, can further envision the provision of fluidic interconnection established between the underlying implant 178 and the reservoir chamber 186.

Figure 37:
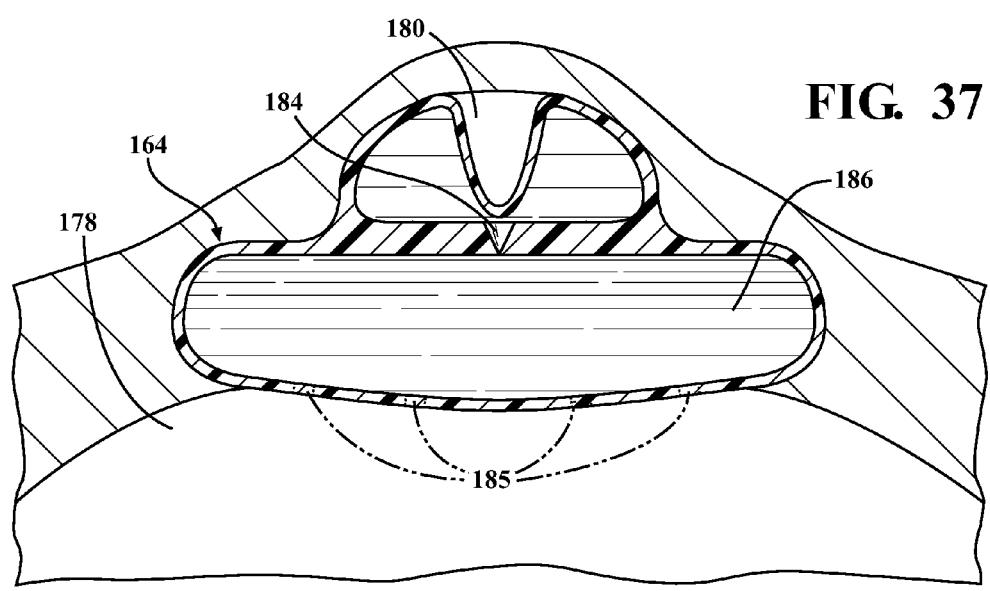
FIG. 37 is a succeeding illustration to FIG. 36 and depicting another variant of fluid transfer nipple in which fluid flow is initiated through squeezing of the breast implant outside of the areola in order to cause fluid to flow from the reservoir chamber to the extender chamber.

FIG. 37 is a succeeding illustration to FIG. 36 and depicting another variant of fluid transfer nipple in which fluid flow is initiated through squeezing of the breast implant 178 outside of the areola location 164, this in order to cause fluid to flow from the reservoir chamber 186 to the extender chamber 180. As previously described, this can envisioned a fluid interconnection established between the underlying implant 178 which passes fluid into a vent or aperture (or any arrangement of apertures as depicted by non limiting example at 185) and interconnecting the nipple reservoir chamber 186 with the main fluid holding reservoir associated with the main breast implant 178. Alternatively, the reservoir chamber can be mounted to the surface of the main breast implant and while maintaining a separate fluid pressurization which is triggered with or without depressing of or stimulation to the main breast implant.

Figure 38:
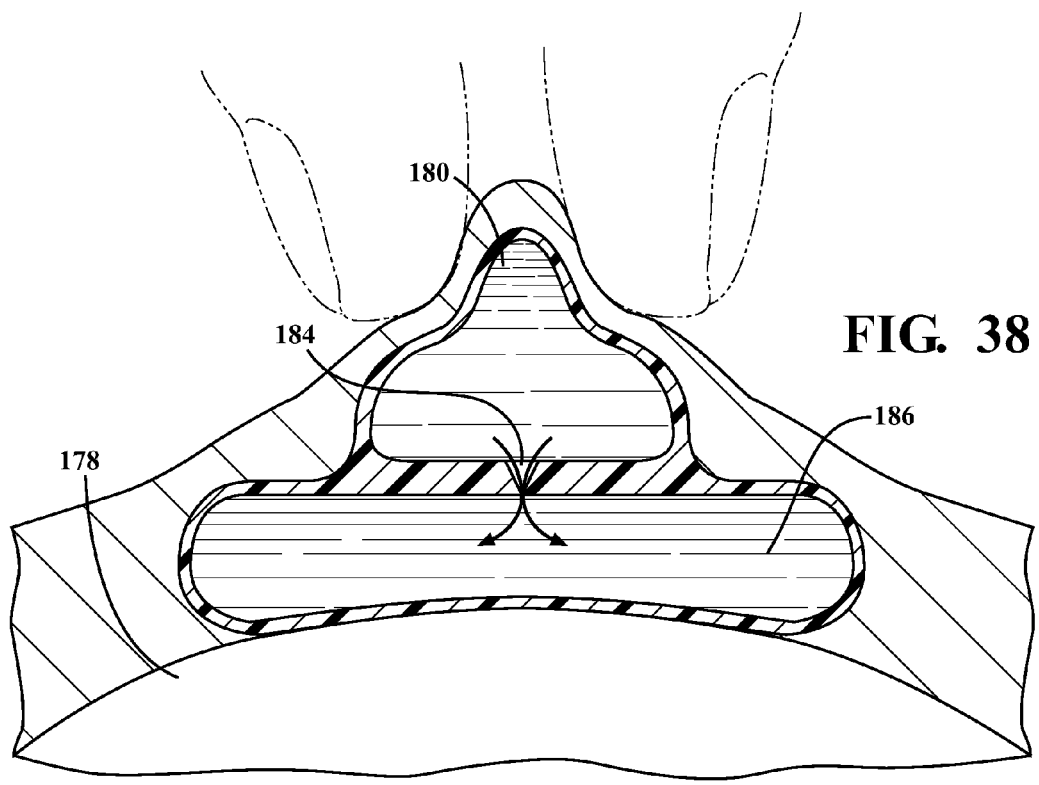
FIG. 38 is a succeeding illustration in which the squeezing of the extended nipple chamber overpowers the interconnecting check valve and results in the return of fluid to the annular reservoir chamber, with additional slow leak return features also capable of being designed into the nipple implant.
Figure 39:
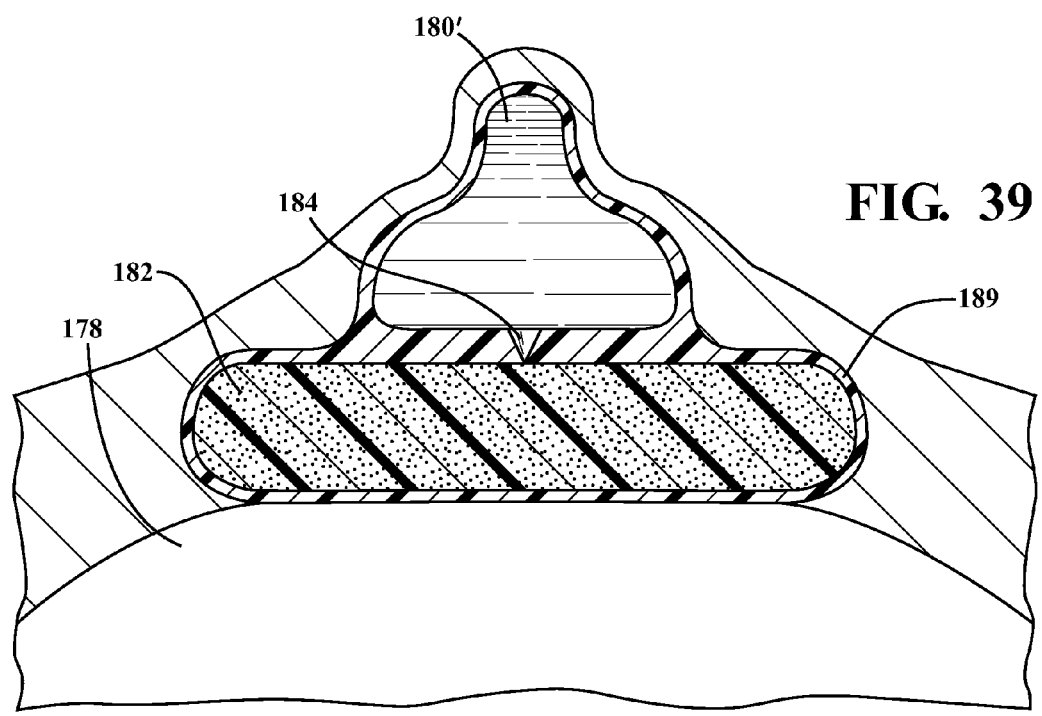
FIG. 39 is an illustration of a sponge reservoir chamber incorporated into a surface mounted nipple implant as depicted in FIG. 38.

FIG. 38 is a succeeding illustration to FIG. 37 (and generally similar to as previously shown in FIG. 36) in which the squeezing of extended nipple chamber 180' overpowers the interconnecting check valve 184 operating in a first configuration to maintain fluid within the extender chamber 180', and results in the return of fluid to the annular reservoir chamber, 186, with additional slow leak return features also capable of being designed into the nipple implant in order to control the rate of retraction of the nipple chamber. FIG. 39 is an illustration of a sponge reservoir chamber, again such as depicted at 182, incorporated into a surface mounted nipple implant as depicted in FIG. 38 and which operates in a similar fashion as previously described in which squeezing of the breast implant 178 causes fluid from the reservoir chamber 182 to transfer to the extender chamber 180', with a further time release sponge re-inflation (resulting from reverse flow of fluid) causes collapse of the extender nipple chamber to the return retracted position. As further depicted in FIG. 39, an outer plastic or silicon layer (see at 189) can encase the annular or other shaped reservoir 182 (such as in particular the sponge configured chamber) and nipple extender chamber 180 in order to facilitate fluid flow therebetween.

Figure 40:
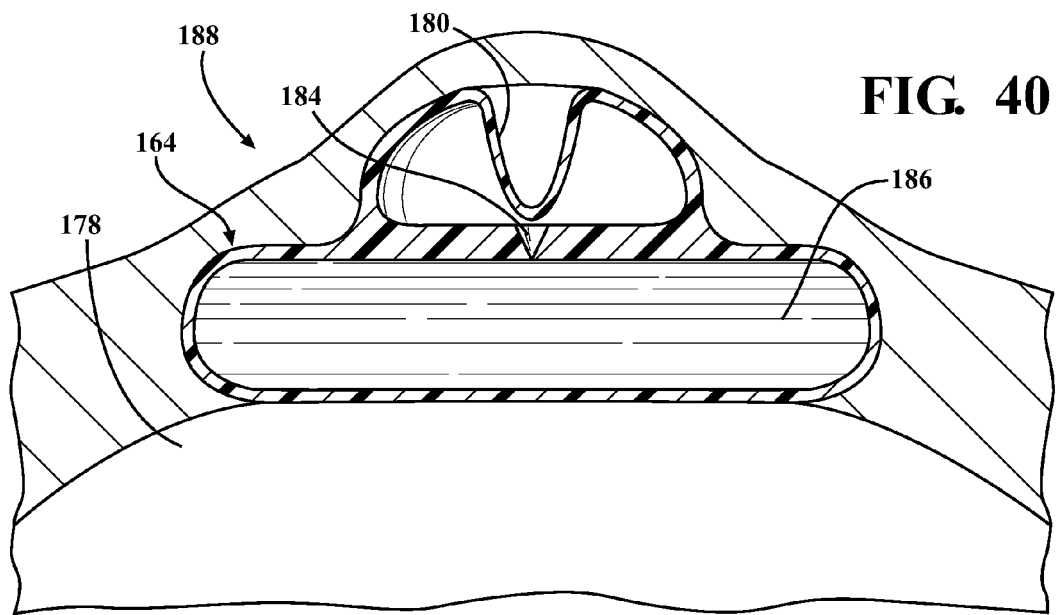
FIG. 40 is an illustration of a further pressurized nipple implant similar to that previously described and which is mounted to a surface of the underlying breast implant.

FIG. 40 is an illustration 188 of a further pressurized nipple implant similar to that previously described and which is again mounted to a surface of the underlying breast implant 178. Operative manipulation by pressing upon the surrounding areola location (again referenced by location 164) results in transfer of fluid to the extender chamber as further again shown in relaxed (inverted) position at 180, the extender chamber subsequently capable of being collapsed with a minimal amount of fluid transfer.

Figure 41:
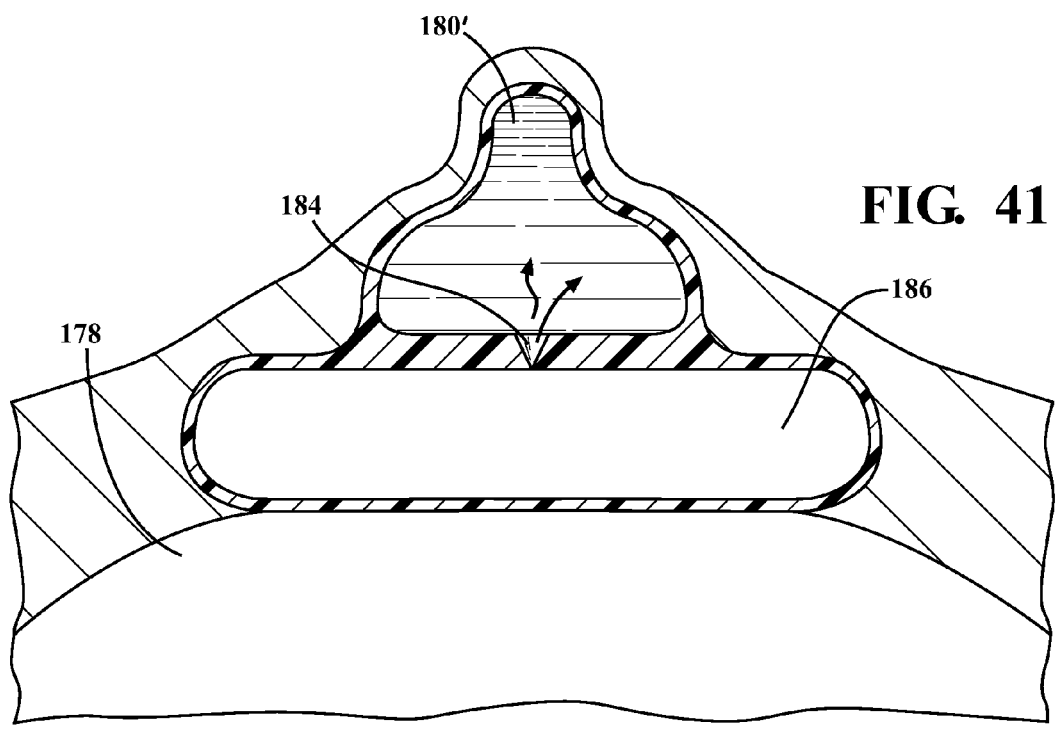
FIG. 41 is an illustration of a two way fluid flow arrangement established between the reservoir and nipple extender chambers of a breast implant surface mounted configuration of nipple implant and which again depicts the squeezing the nipple extender chamber for transferring fluid in re-pressurizing fashion back into a reservoir chamber, return expanding flow into the nipple chamber again resulting from pressing of the underlying breast, thus triggering a stop valve between the fluidly interconnected reservoir chamber and nipple chamber to cause re-inflation of the nipple chamber.

FIG. 41 is an illustration of a two way fluid flow arrangement established between the reservoir 186 and nipple 180' extender chambers of a breast implant 167 surface mounted configuration of nipple implant and which again depicts the squeezing the nipple extender chamber (including nipple and/or surrounding areola) for causing transfer of fluid in re-pressurizing fashion back into a reservoir chamber, return expanding flow into the nipple chamber again resulting from pressing of the underlying breast, thus triggering stop valve 184 positioned between the fluidly interconnected reservoir chamber and nipple chamber to cause re-inflation of the nipple chamber. A separate check valve may also be included to maintain fluid pressure in either of the reservoir or extended nipple chambers and which can be triggered by manipulative pressure exerted by a user.

Figure 42:
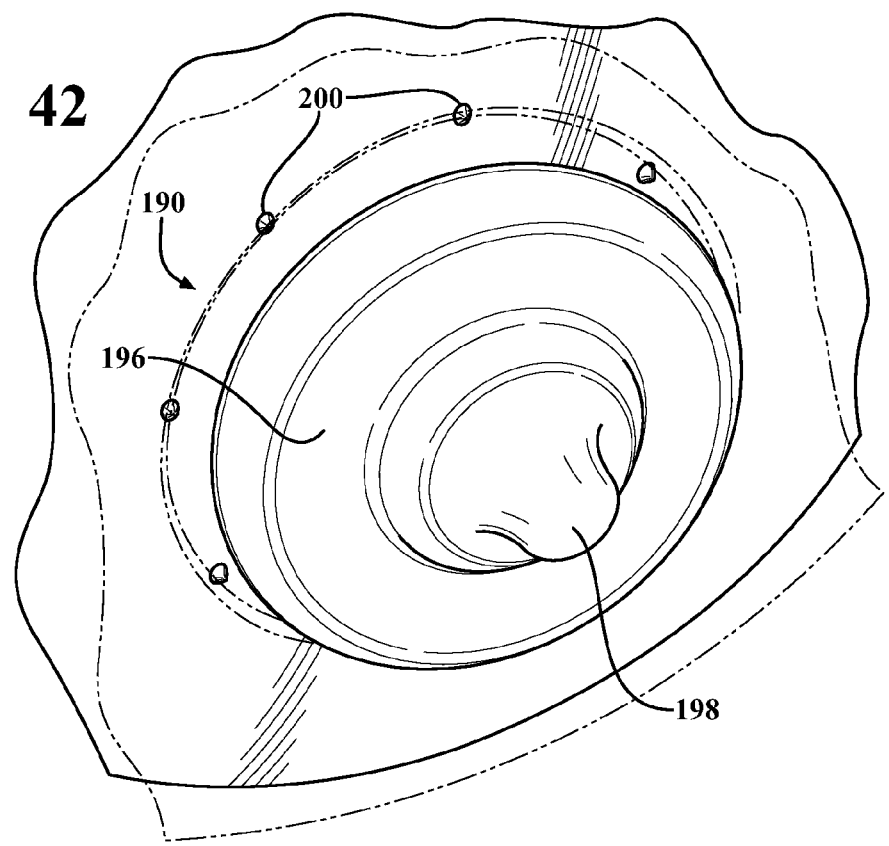
FIG. 42 is a perspective view of a breast reconstructive or augmented implant exhibiting a surface repositionable and releasably fixable nipple.
Figure 43:
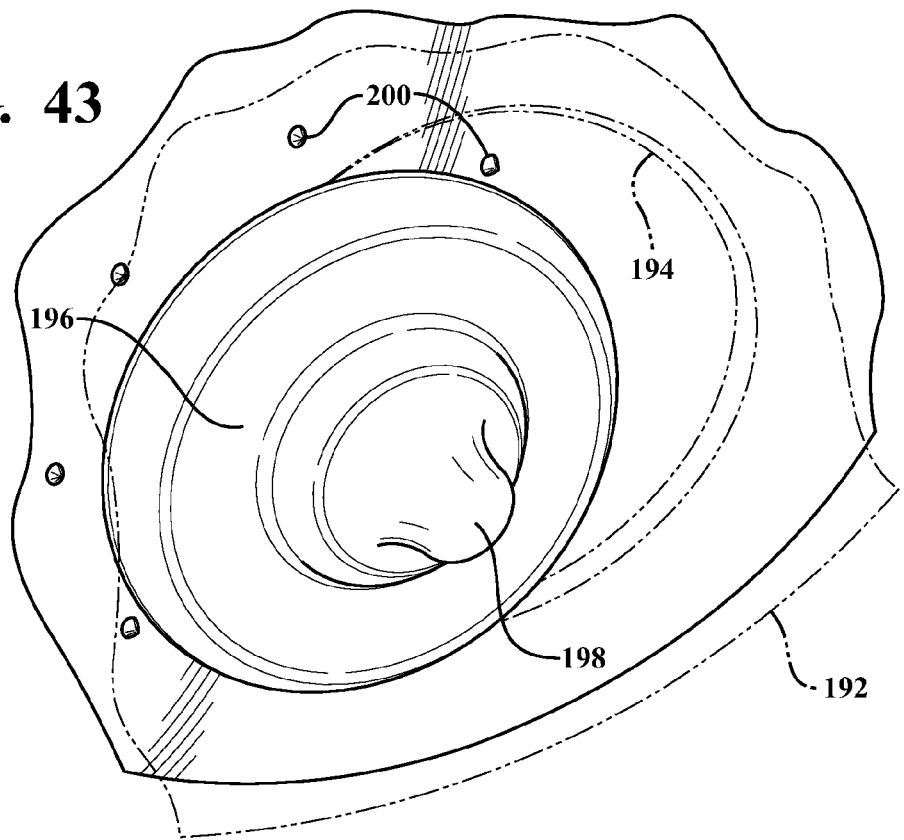
FIG. 43 is a succeeding illustration depicting a range of offset adjustability exhibited by the surface repositionable nipple relative to a stationary overlay with central circular aperture.
Figure 44:
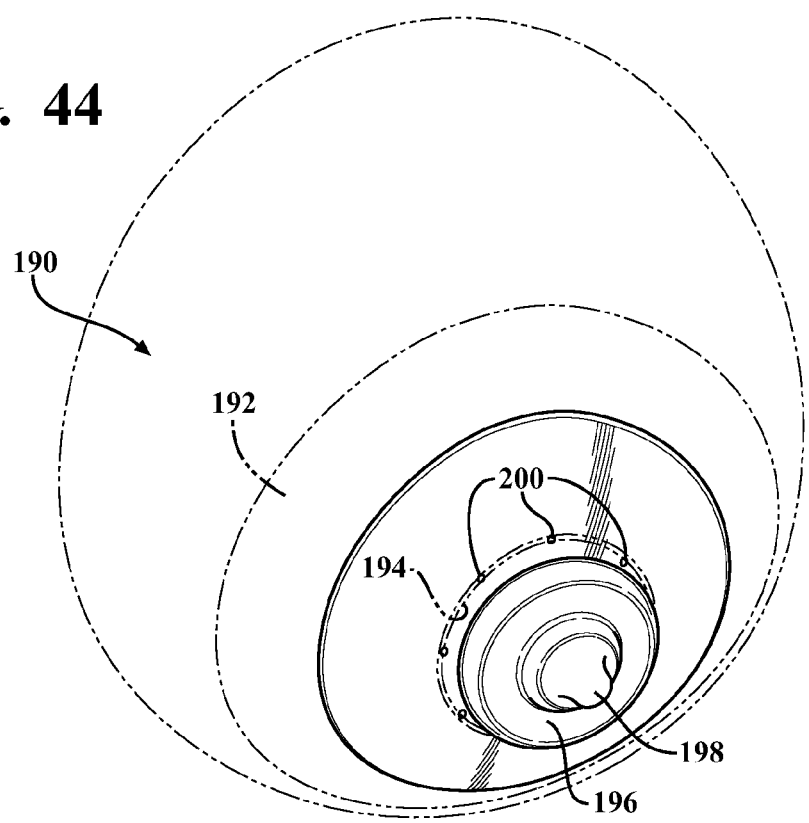
FIG. 44 is an enlarged perspective view of the implant in FIG. 42.
Figure 45:
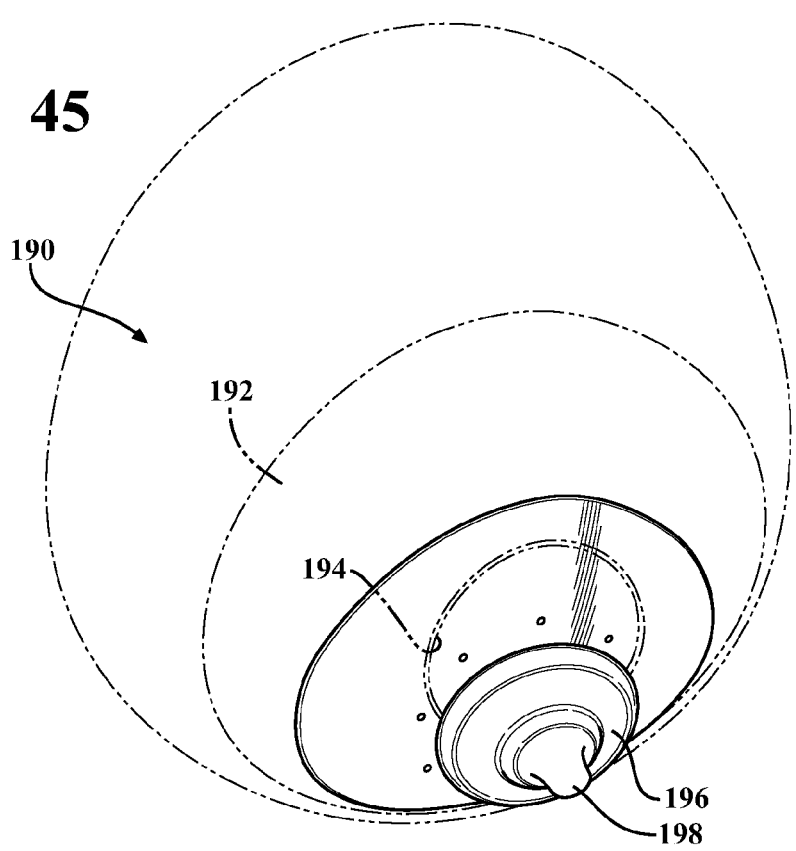
FIG. 45 is a view similar to FIG. 44 and illustrating the nipple in repositioned fashion.

FIGS. 42-47 illustrate a further variant of a breast reconstructive or augmented implant exhibiting a surface repositionable and releasably fixable nipple. FIG. 42 is a perspective view of the implant, generally at 190, exhibiting a surface repositionable and releasably fixable nipple. The implant is constructed similar to any of those previously described. A fixed pseudo lens overlay 192 (best illustrated in side cutaway in FIGS. 46-47) extends across a convex surface associated with the implant (see as shown in each of FIGS. 44-47) and exhibits an inner perimeter extending surface 194 defining a generally central circular aperture through which projects surface supported nipple.

The nipple again includes both a supporting areola 196 (either pre-pressurized or providing a pump action) and for selectively inflating or deflating a central projecting portion 198. As further depicted in each of the figures, a range of offset adjustability is afforded the surface supported nipple relative to the stationary lens overlay with central circular aperture.

Figure 46:
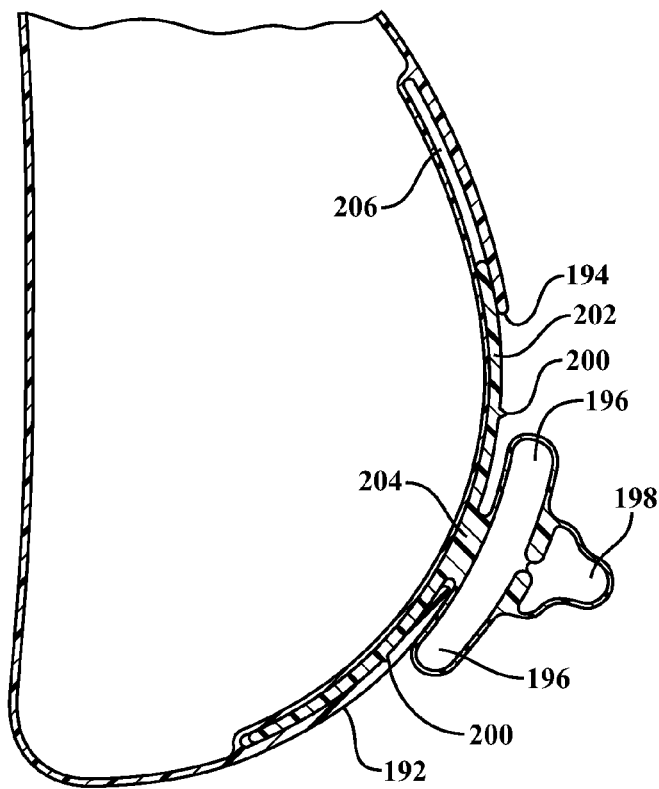
FIG. 46 is a side cutaway line art view depicting the surface repositionable nipple associated with the underlying implant with stationary overlay and further depicting the press engageable locking prongs for securing the nipple at a lower displaced position.
Figure 47:
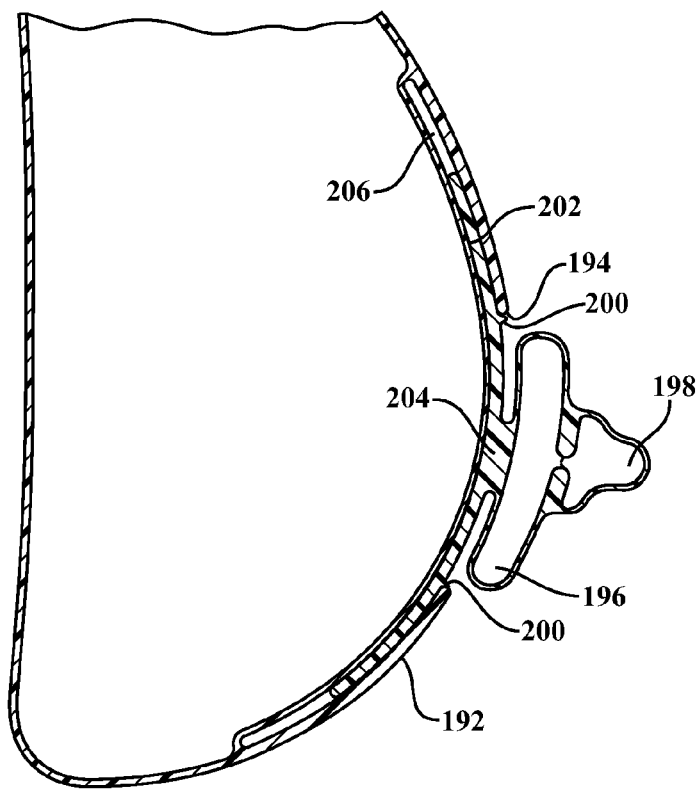
FIG. 47 is a succeeding side cutaway line art view depicting the nipple in a substantially central position.

FIG. 46 is a side cutaway line art view depicting the surface repositionable nipple associated with the underlying implant with stationary overlay 192. As best shown in FIGS. 46 and 47, a plurality of press engageable locking prongs 200 each project from intermediate diameter locations of a perimeter skirt 202 which in turn extends from an underside support 204 secured to the nipple.

In this fashion, and as further evident from reference to each of the side cutaway views of FIGS. 46 and 47, the nipple is displaced to any offset location afforded by the range defined by the inner perimeter 194 of the lens overlay 192. Upon achieving a desired (re)position, the lens 192 is pressed inwardly such that the underside positioned and projecting prongs associated with the seated perimeter skirt 202 engages within the underside of the surface lens 192 (see in particular each of the FIGS. 46 and 47) in order to fix the nipple in position. As further depicted in each of FIGS. 46 and 47, a concave pocket 206 is established between a base surface of the implant and the surface overlaying lens 192 within which the underlying skirt 202 of the nipple is seated in a limited offset repositionable nature.

Having described my invention, other and additional preferred embodiments will become apparent to those skilled in the art to which it pertains, and without deviating from the scope of the appended claims.

I claim:

1. A combination breast and nipple implant, comprising:
   a first fluid holding and flexible breast implant body;
   a second nipple implant body having a reservoir chamber and an interconnected extender chamber upon which is mounted a flexible nipple;
   said nipple implant body mounted atop said breast implant body such that said nipple is repositionable along a limited arcuate surface of said breast implant body; and
   a convex and perimeter extending skirt extending from said repositionable nipple implant body and which is seated within an arcuate and perimeter extending pocket defined between a surface of said breast implant body and an overlaying lens, an inner perimeter edge of said lens defining a maximum range of eccentric adjustment.

2. The implant as described in claim 1, at least one of said breast implant body and said nipple implant body further comprising at least one of a plasticized, silicone or sponge construction.

3. The implant as described in claim 1, further comprising a plurality of press engageable locking prongs projecting from intermediate diameter locations of said perimeter extending skirt and, upon adjusting said nipple implant body in a given arcuate direction, contacting said inner perimeter edge of said lens.

4. A combination breast and nipple implant, comprising:
   a first fluid holding and flexible breast implant body;
   a second nipple implant body arcuately repositionable mounted atop said breast implant body, said nipple implant body having an areola replicating reservoir chamber communicating with an outermost projecting and inflatable nipple replicating portion;

upon pressurizing said areola replicating chamber, manipulation of a communicating valve passageway inflating said nipple replicating portion, subsequent pinching of said nipple replicating portion causing deflation thereof with return pressurized flow into said areola replicating chamber; and convex and perimeter extending skirt extending from said repositionable nipple implant body and which is seated within an arcuate and perimeter extending pocket defined between a surface of said breast implant body and an overlaying lens, an inner perimeter edge of said lens defining a maximum range of eccentric adjustment.

5. The combination implant as described in claim 4, at least one of said breast implant body and said nipple implant body further comprising at least one of a plasticized, silicone or sponge construction.

6. The implant as described in claim 4, further comprising a plurality of press engageable locking prongs projecting from intermediate diameter locations of said perimeter extending skirt and, upon adjusting said nipple implant body in a given arcuate direction, contacting said inner perimeter edge of said lens.

* * * * *